(12) United States Patent
Park et al.

(10) Patent No.: US 12,325,694 B2
(45) Date of Patent: Jun. 10, 2025

(54) CO-CRYSTALLINE FORM OF EFINACONAZOLE AND METHOD FOR PREPARING THE SAME

(71) Applicant: Daebong Ls Co., Ltd., Incheon (KR)

(72) Inventors: Eun Ju Park, Hwaseong-si (KR); Hyun Ji, Siheung-si (KR); Eun Mi Kim, Incheon (KR); Jin Oh Park, Seoul (KR)

(73) Assignee: DAEBONG LS CO., LTD., Incheon (KR)

( * ) Notice: Subject to any disclaimer, the term of this patent is extended or adjusted under 35 U.S.C. 154(b) by 943 days.

(21) Appl. No.: 17/428,426

(22) PCT Filed: Sep. 25, 2020

(86) PCT No.: PCT/KR2020/013163
§ 371 (c)(1),
(2) Date: Aug. 4, 2021

(87) PCT Pub. No.: WO2021/060949
PCT Pub. Date: Apr. 1, 2021

(65) Prior Publication Data
US 2022/0194919 A1 Jun. 23, 2022

(30) Foreign Application Priority Data
Sep. 26, 2019 (KR) .................. 10-2019-0118646

(51) Int. Cl.
C07D 401/06 (2006.01)
A61K 31/454 (2006.01)

(52) U.S. Cl.
CPC ........ C07D 401/06 (2013.01); *C07B 2200/13* (2013.01)

(58) Field of Classification Search
CPC ...... C07D 401/06; A61K 31/454; A61P 31/10
USPC .......................................... 546/210; 514/326
See application file for complete search history.

(56) References Cited

U.S. PATENT DOCUMENTS

| 5,620,994 | A | 4/1997 | Naito et al. |
| 8,486,978 | B2 | 7/2013 | Winckle et al. |
| 2020/0078347 | A1* | 3/2020 | Mizutani et al. .... A61K 31/454 514/326 |

FOREIGN PATENT DOCUMENTS

| CN | 106995434 A | 8/2017 |
| JP | 2005-535602 A | 11/2005 |
| JP | 2008-503495 A | 2/2008 |
| JP | 2010-522153 A | 7/2010 |
| JP | 2016-532722 A | 10/2016 |
| KR | 10-2016-0068812 A | 6/2016 |
| WO | WO 2004/078163 A1 | 9/2004 |
| WO | WO 2004/078163 A2 | 9/2004 |
| WO | WO 2010/034976 A2 | 4/2010 |
| WO | WO 2013/084130 A1 | 6/2013 |
| WO | WO 2016/116919 A1 | 7/2016 |
| WO | WO 2016/193917 A1 | 12/2016 |
| WO | WO 2018/036416 A1 | 3/2018 |

OTHER PUBLICATIONS

Owoyemi et al., Cryst. Growth Des., 19, 648-657 (2019).
Shevchenko et al., Cryst. Growth Des., A-H (Sep. 2013).
International Search Report dated Jan. 13, 2021 for PCT/KR2020/013163.
Hilfiker, et al. "Relevance of Solid-state Properties for Pharmaceutical Products", Polymorphism in the Pharmaceutical Industry, 2006.
Owoyemi et al. "Fluconazole: Synthesis and Structural Characterization . . . etc.", Crystal Growth & Design , 2019.

* cited by examiner

*Primary Examiner* — Charanjit Aulakh
(74) *Attorney, Agent, or Firm* — Lee IP Law, P.C.

(57) ABSTRACT

The present invention relates to a co-crystalline form of efinaconazole and a pharmaceutically acceptable coformer forming a co-crystalline phase. The present invention also relates to a method for preparing the co-crystalline form. The co-crystallization product of efinaconazole according to the present invention meets all requirements for use as an active ingredient of a pharmaceutical composition and is highly stable to heat and other one or more other ingredients of the composition. Therefore, the co-crystallization product of efinaconazole is suitable for use in the preparation of pharmaceuticals. In addition, the method of the present invention enables the preparation of the co-crystallization product of efinaconazole in a simple and easy manner on a commercial scale.

8 Claims, 26 Drawing Sheets

CO-CRYSTALLINE FORM OF EFINACONAZOLE AND METHOD FOR PREPARING THE SAME

CROSS REFERENCE TO RELATED APPLICATIONS

This is the U.S. national phase application based on PCT Application No. PCT/KR2020/013163, filed Sep. 25, 2020, which is based on Korean Patent Application No. 10-2019-0118646, filed Sep. 26, 2019, the entire contents of all of which are hereby incorporated by reference.

TECHNICAL FIELD

The present invention relates to a co-crystalline form of efinaconazole and a method for preparing the same.

BACKGROUND ART

External antifungal agents, including amorolfine, ciclopirox, and efinaconazole, have been used to treat onychomycosis. Amorolfine and efinaconazole exhibit antifungal activities to inhibit the synthesis of ergosterol, an essential constituent of the fungal cell membrane. Ciclopirox exhibits antifungal activity to block the biosynthesis of DNA, RNA, and protein by interfering with $Na^+/K^+$ ATPase carrying substances (e.g., amino acids) or ions (e.g., potassium ions) essential for cells in the fungal cell membrane.

Among these drugs, efinaconazole (CAS No. 164650-44-6) is a triazole compound with proven therapeutic activity for onychomycosis.

Formulations useful for topical delivery of efinaconazole and other triazole antifungal drugs for the treatment of onychomycosis are described, for example, in U.S. Pat. No. 8,486,978 (Patent Document 1).

However, some formulations containing the triazole active ingredients exhibit varying degrees of instability during storage.

That is, certain formulations are known to exhibit discoloration within storage periods as short as 1 or 2 days, resulting in solutions ranging in color from yellow to deep red or brown (KR2016-0068812 A; Patent Document 2).

Due to its instability, efinaconazole needs to be converted to a stable crystalline form of efinaconazole for use as an active ingredient of a pharmaceutical composition.

Many methods for preparing polymorphs and p-toluenesulfonate of efinaconazole have been reported thus far (see, for example, U.S. Pat. No. 5,620,994 (Patent Document 3)).

However, polymorphs and p-toluenesulfonate of efinaconazole are not satisfactory in terms of stability. The development of stable forms of efinaconazole is still one of the challenging issues in this field.

Thus, there exists a need for a stabilized formulation of efinaconazole. The present inventors have conducted research on a method for preparing a co-crystalline form of efinaconazole, a therapeutic agent for onychomycosis, that can be prepared into a formulation stable to heat and one or more other ingredients of the composition.

(Patent Document 1) U.S. Pat. No. 8,486,978 B2 (Jul. 16, 2013)
(Patent Document 2) Korean Patent Publication No. 2016-0068812 A (Jun. 15, 2016)
(Patent Document 3) U.S. Pat. No. 5,620,994 A (Apr. 15, 1997)

DETAILED DESCRIPTION OF THE INVENTION

Problems to be Solved by the Invention

It is an object of the present invention to provide a novel co-crystalline form of efinaconazole and a method for preparing the same.

Means for Solving the Problems

The present invention has been made in an effort to solve the problems of the prior art and provides a co-crystallization product of efinaconazole and a pharmaceutically acceptable coformer forming a co-crystalline phase.

In the present invention, the coformer is selected from polyethylene glycol, nicotinamide, fumaric acid, hydroquinone, malonic acid, caffeic acid, and mixtures thereof.

In the present invention, the polyethylene glycol is polyethylene glycol-6000.

In the present invention, the coformer is polyethylene glycol and the powder X-ray diffraction (XRD) spectrum of the co-crystallization product has peaks at diffraction angles (2θ) of 7.78°, 11.50°, 13.85°, 15.49°, 16.79°, 18.97°, 19.22°, 23.57°, 26.18°, and 27.09°.

In the present invention, the differential scanning calorimetry (DSC) thermogram of the co-crystallization product has maximum endothermic peaks at 61.62° C. and 78.78° C.

In the present invention, the coformer is caffeic acid and the powder X-ray diffraction (XRD) spectrum of the co-crystallization product has peaks at diffraction angles (2θ) of 13.65°, 14.22°, 15.90°, 17.51°, 17.71°, 19.91°, 20.32°, 20.96°, 24.50°, 25.82°, 26.70°, 27.12°, 27.46°, 30.13°, 33.58°, 35.76°, and 36.59°.

In the present invention, the differential scanning calorimetry (DSC) thermogram of the co-crystallization product has maximum endothermic peaks at 66.45° C. and 179.9° C.

The present invention also provides an oral or parenteral pharmaceutical composition for treating onychomycosis including a co-crystallization product of efinaconazole as an active ingredient.

The present invention also provides a method for preparing a co-crystallization product of efinaconazole including dissolving efinaconazole and a pharmaceutically acceptable coformer in an organic solvent to prepare a mixed solution and evaporating the mixed solution to remove the solvent.

In the present invention, the mixed solution is prepared with stirring or under heating.

In the present invention, the organic solvent is methanol, ethanol, isopropyl alcohol, n-propanol, isoamyl alcohol, acetone, ethyl methyl ketone, methyl isobutyl ketone, ethyl acetate, n-propyl acetate, n-butyl acetate, t-butyl acetate, toluene, dichloromethane, acetonitrile or a mixture thereof.

In the present invention, the coformer is selected from polyethylene glycol, nicotinamide, fumaric acid, hydroquinone, malonic acid, caffeic acid, and mixtures thereof.

The present invention also provides a co-amorphous product of efinaconazole and a pharmaceutically acceptable coformer forming a co-amorphous phase.

In the present invention, the coformer is selected from citric acid, oxalic acid, and a mixture thereof.

Effects of the Invention

The co-crystallization product of efinaconazole according to the present invention meets all requirements for use as an active ingredient of the pharmaceutical composition and is highly stable to heat and other one or more other ingredients of the composition. Therefore, the co-crystallization product of efinaconazole according to the present invention is suitable for use in the preparation of pharmaceuticals. In addition, the method of the present invention enables the preparation of the co-crystallization product of efinaconazole in a simple and easy manner on a commercial scale.

BEST MODE FOR CARRYING OUT THE INVENTION

The present invention will now be described in detail.

One aspect of the present invention is directed to a co-crystallization product of efinaconazole and a pharmaceutically acceptable coformer forming a co-crystalline phase.

A co-formed product is composed of two or more components and exhibits unique physical properties different from those of the individual components, just like a single material. Co-formed products are divided into co-amorphous products and co-crystals.

The term "co-crystal" refers to a crystal structure of two or more different molecules in a specific stoichiometric ratio within one crystal lattice. Intermolecular bonds in co-crystals are distinguished from those in salts and mixtures. A co-crystal is a crystalline solid that is rich in functional groups (for example, O, OH, and N) capable of hydrogen bonding or has a new crystal structure through hydrogen bonding with a coformer in a regular ratio.

The term "coformer" refers to an inactive molecule constituting a co-crystal of a drug.

As described above, efinaconazole needs to be converted to a stable crystalline form of efinaconazole for use as an active ingredient of a pharmaceutical composition due to its instability. Since a co-crystal of a drug forms a crystal structure through a new hydrogen bond between two or more molecules, the solubility and dissolution rate of the drug can be increased while maintaining the stable state of the co-crystal, and as a result, the uptake of the drug is altered, leading to a change in the bioavailability of the drug.

Although the existence of some co-crystallization products is already known, their proportion is less than 1% of all general organic compounds. Studies on co-crystallization products are still in the early stages, and particularly, no research has been conducted on co-crystallization products of efinaconazole.

Under such circumstances, the present inventors have found that a co-crystal of efinaconazole meets requirements in terms of physical properties for use as an active ingredient and has good thermal stability. The present invention has been accomplished based on this finding.

The coformer may be selected from polyethylene glycol, nicotinamide, fumaric acid, hydroquinone, malonic acid, caffeic acid, and mixtures thereof. The coformer is preferably selected from polyethylene glycol, nicotinamide, caffeic acid, and mixtures thereof. The coformer is more preferably selected from polyethylene glycol, caffeic acid, and mixtures thereof.

The polyethylene glycol is preferably polyethylene glycol-6000.

Figure 1:
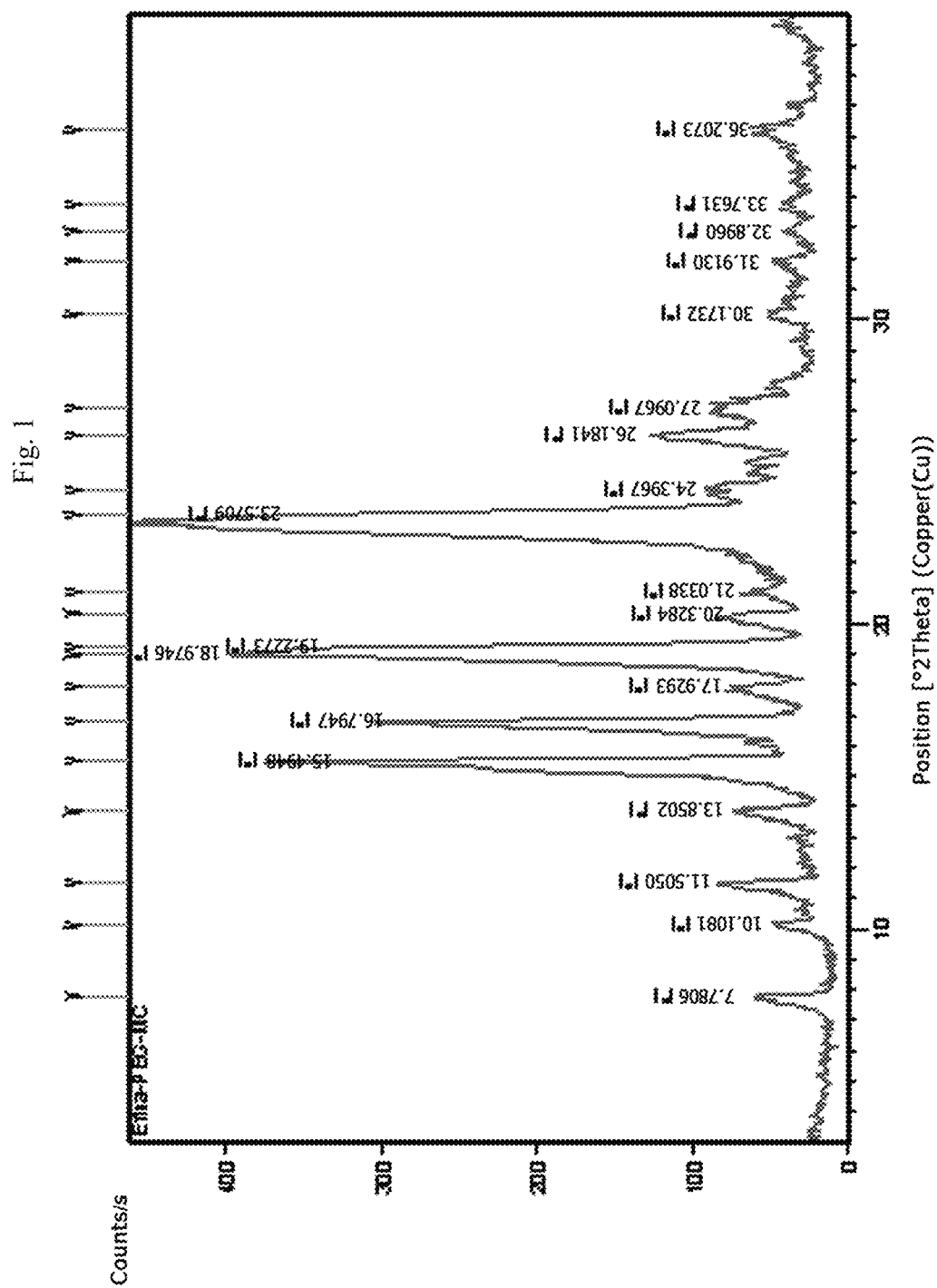
FIG. 1 is a powder XRD pattern of a co-crystal of efinaconazole and polyethylene glycol-6000.
Figure 2:
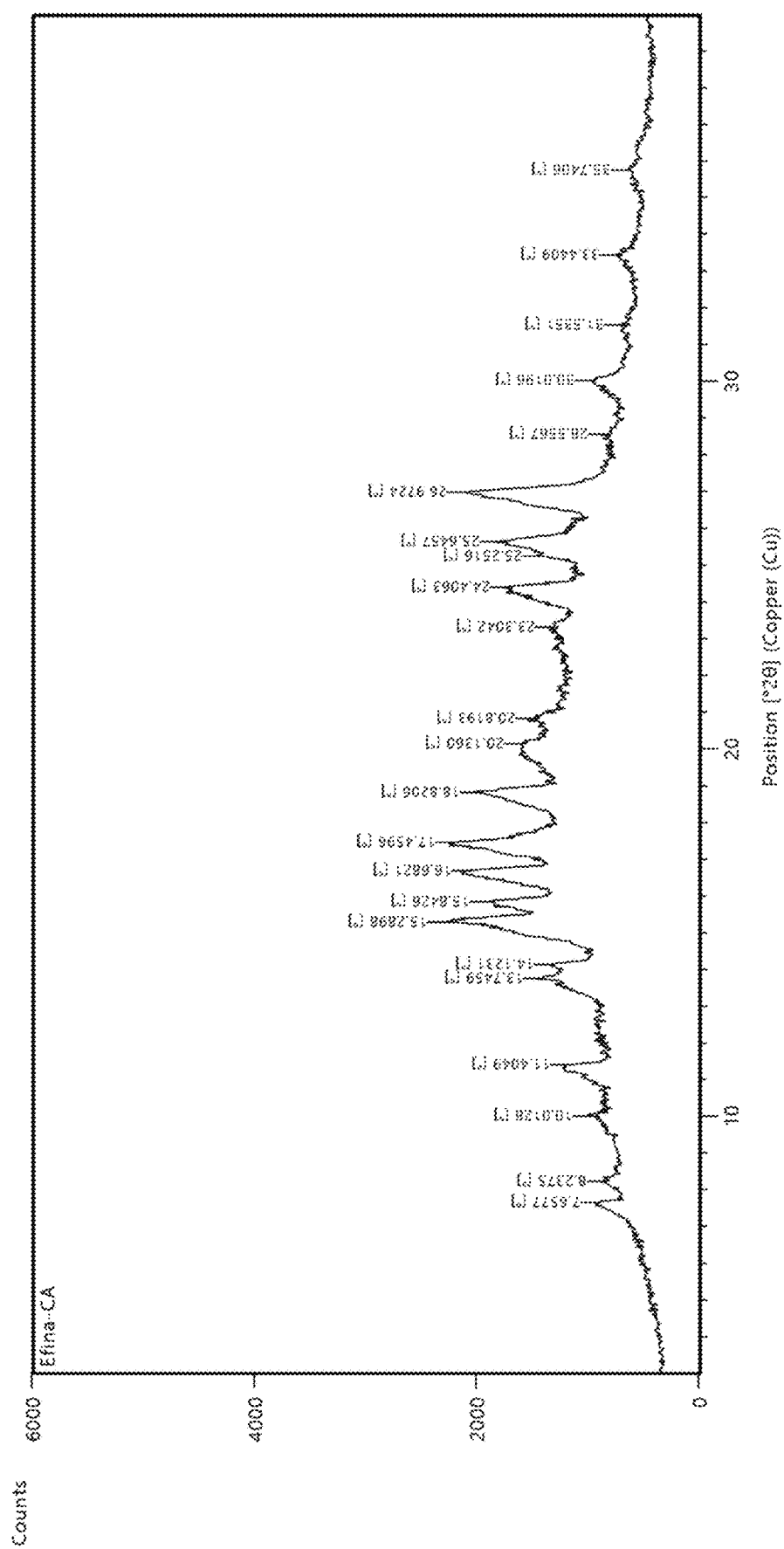
FIG. 2 is a powder XRD pattern of a co-crystal of efinaconazole and caffeic acid.
Figure 3:
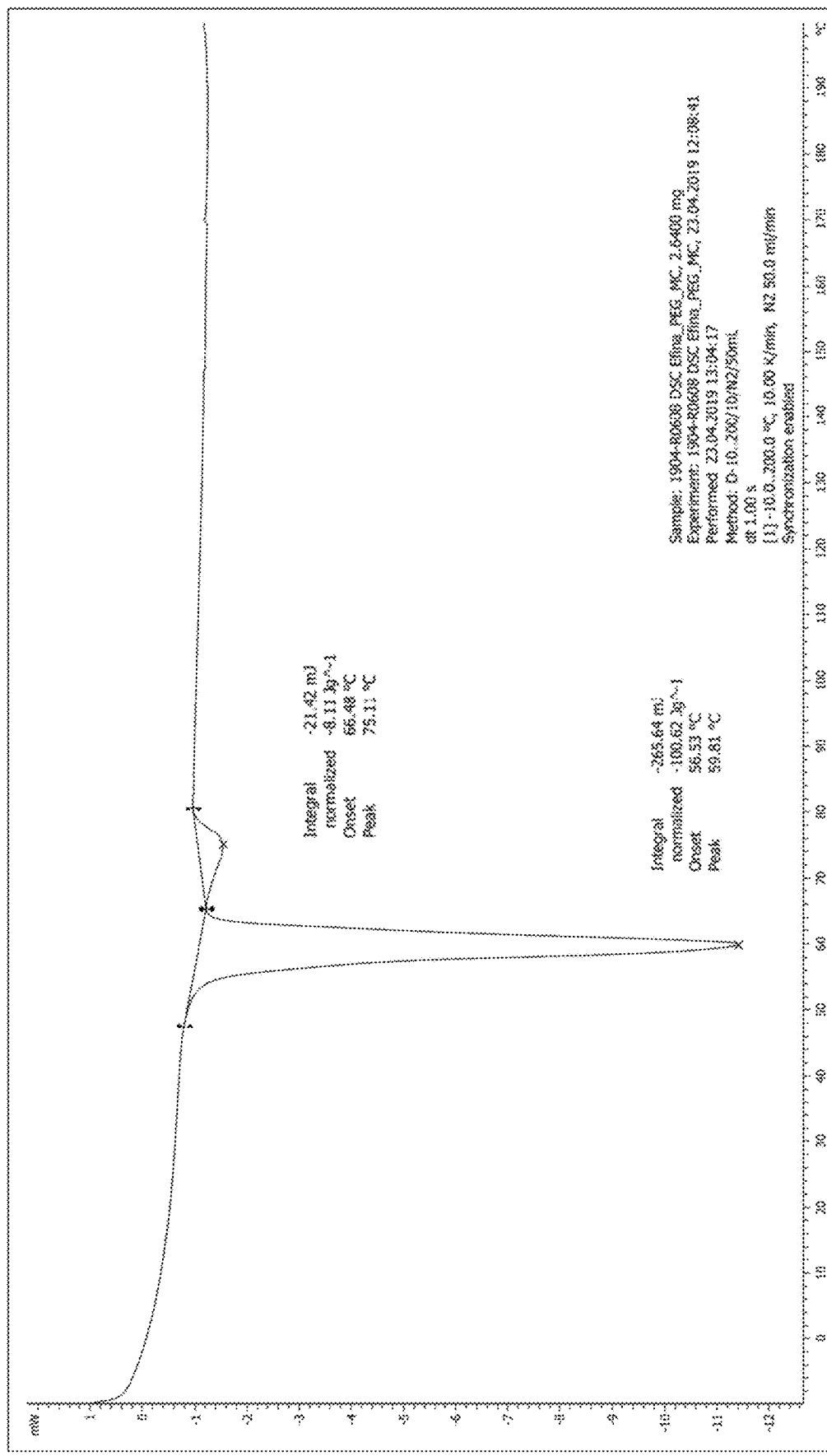
FIG. 3 is a DSC thermogram of a co-crystal of efinaconazole and polyethylene glycol-6000.
Figure 4:
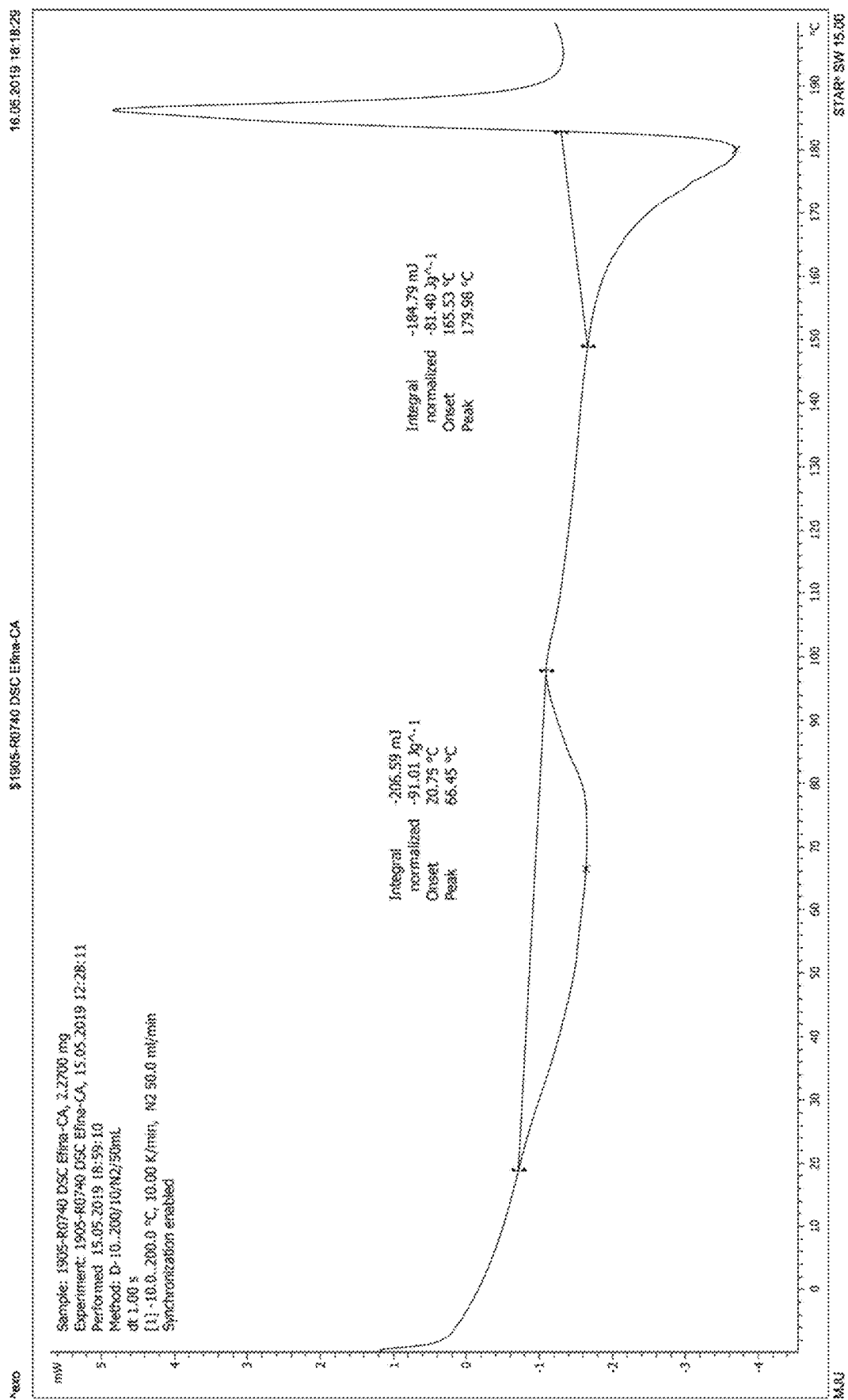
FIG. 4 is a DSC thermogram of a co-crystal of efinaconazole and caffeic acid.

FIGS. 1 and 2 are powder XRD patterns of co-crystals of efinaconazole according to exemplary embodiments of the present invention. FIGS. 3 and 4 are DSC thermograms of co-crystals of efinaconazole according to exemplary embodiments of the present invention.

FIGS. 1 to 4 reveal that the co-crystals of efinaconazole exhibit completely different tendencies from a crystalline form or p-toluenesulfonate of efinaconazole.

That is, the co-crystal of efinaconazole and polyethylene glycol has a crystal structure that exhibits characteristic peaks at diffraction angles (2θ, I/I0>10%) of 7.78°, 11.50°, 13.85°, 15.49°, 16.79°, 18.97°, 19.22°, 23.57°, 26.18°, and 27.09° in its powder XRD pattern.

The differential scanning calorimetry (DSC) thermogram of the co-crystal of efinaconazole and polyethylene glycol has maximum endothermic peaks at 61.62° C. and 78.78° C.

The co-crystal of efinaconazole and caffeic acid has a crystal structure that exhibits characteristic peaks at diffraction angles (2θ, I/I0>10%) of 13.65°, 14.22°, 15.90°, 17.51°, 17.71°, 19.91°, 20.32°, 20.96°, 24.50°, 25.82°, 26.70°, 27.12°, 27.46°, 30.13°, 33.58°, 35.76°, and 36.59° in its powder XRD pattern.

The differential scanning calorimetry (DSC) thermogram of the co-crystal of efinaconazole and caffeic acid has maximum endothermic peaks at 66.45° C. and 179.9° C.

Figure 5:
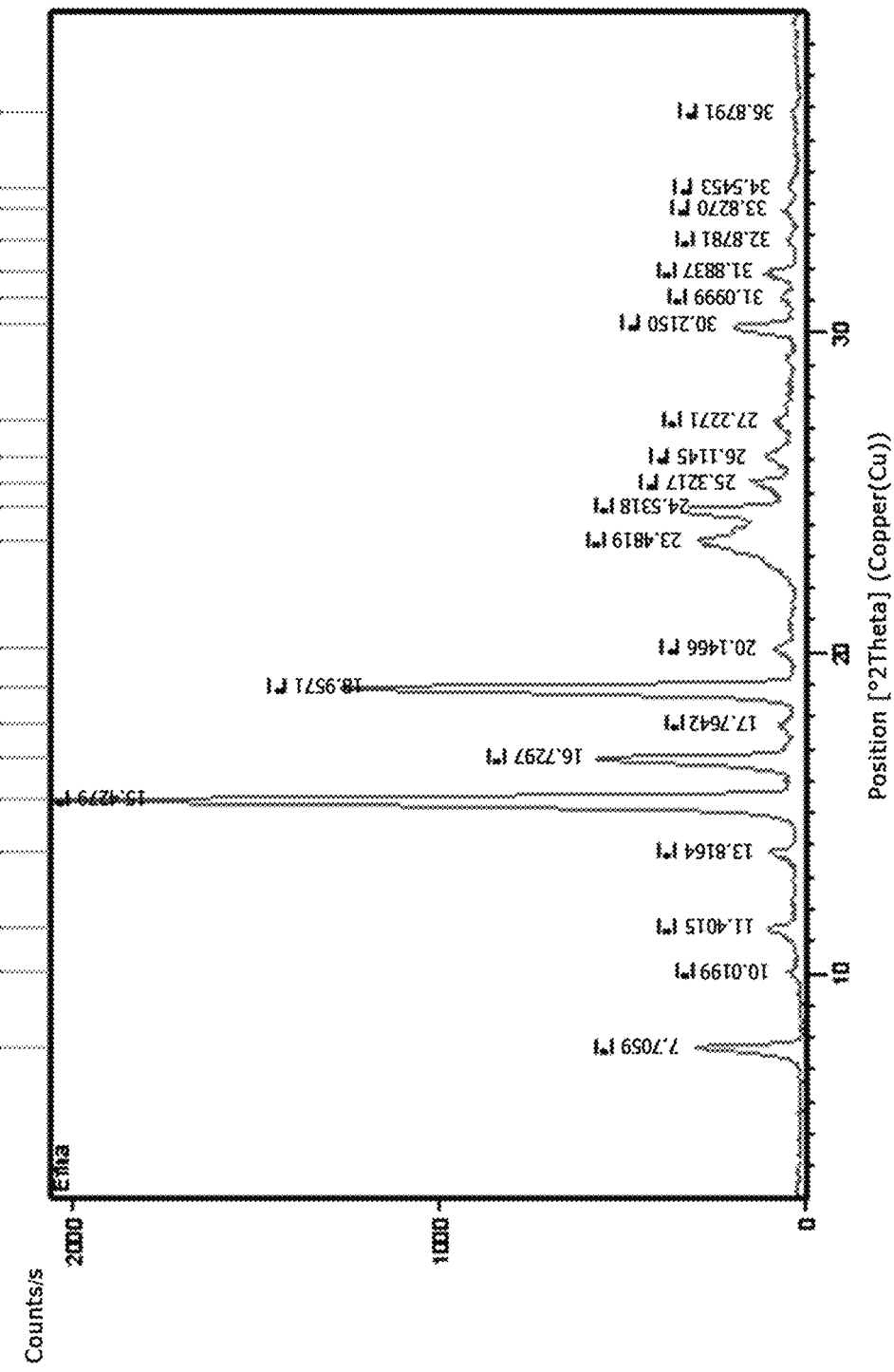
FIG. 5 is a powder XRD pattern of a crystalline form of efinaconazole.
Figure 6:
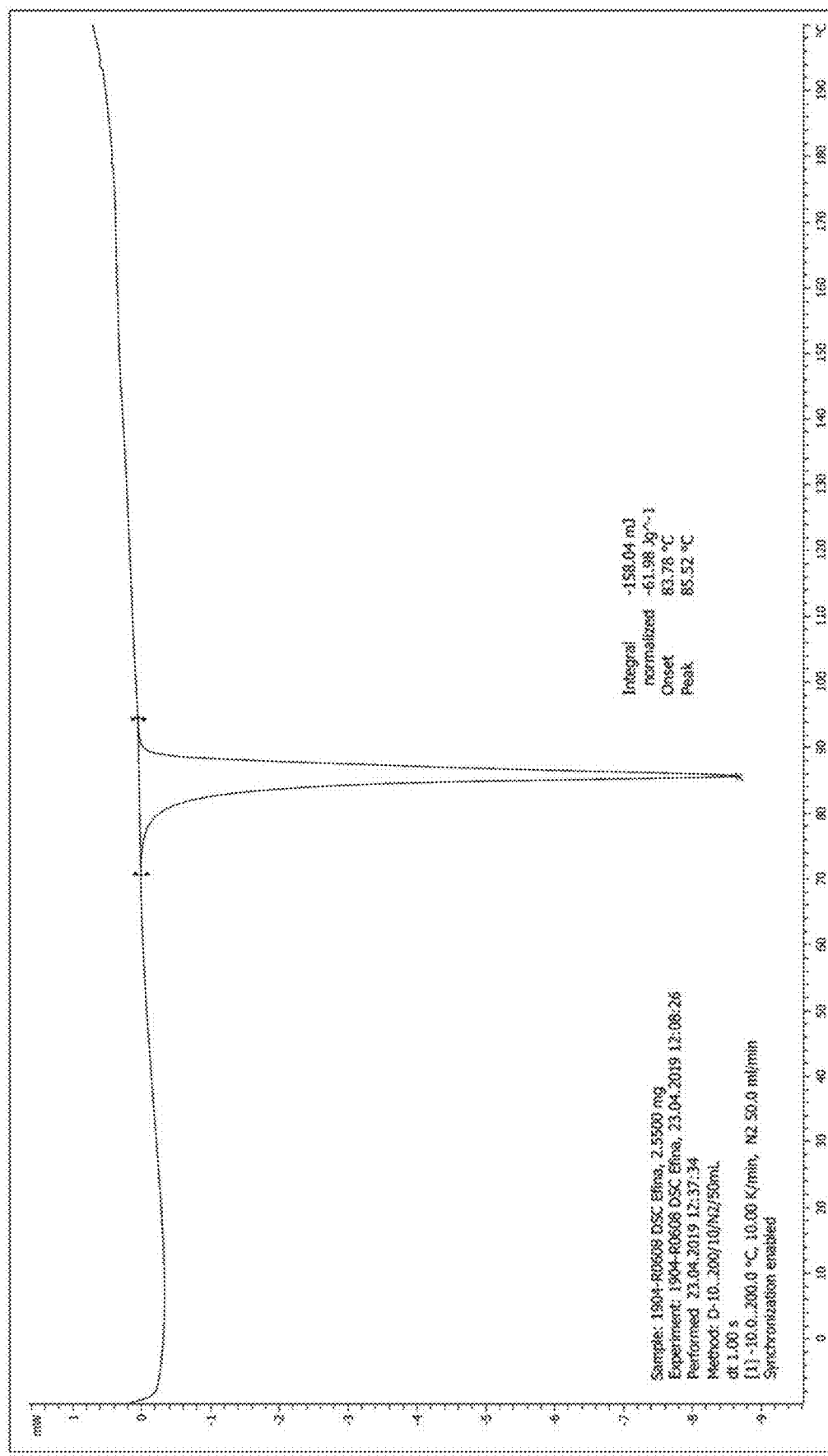
FIG. 6 is a DSC thermogram of a crystalline form of efinaconazole.

These differences can be understood with reference to FIGS. 5 and 6. FIGS. 5 and 6 are a powder XRD pattern and a DSC thermogram of the crystalline form of efinaconazole.

The analyses reveal that the co-crystal of efinaconazole according to the present invention is a novel material having physicochemical properties entirely different from those of existing crystalline forms of efinaconazole.

Figure 7:
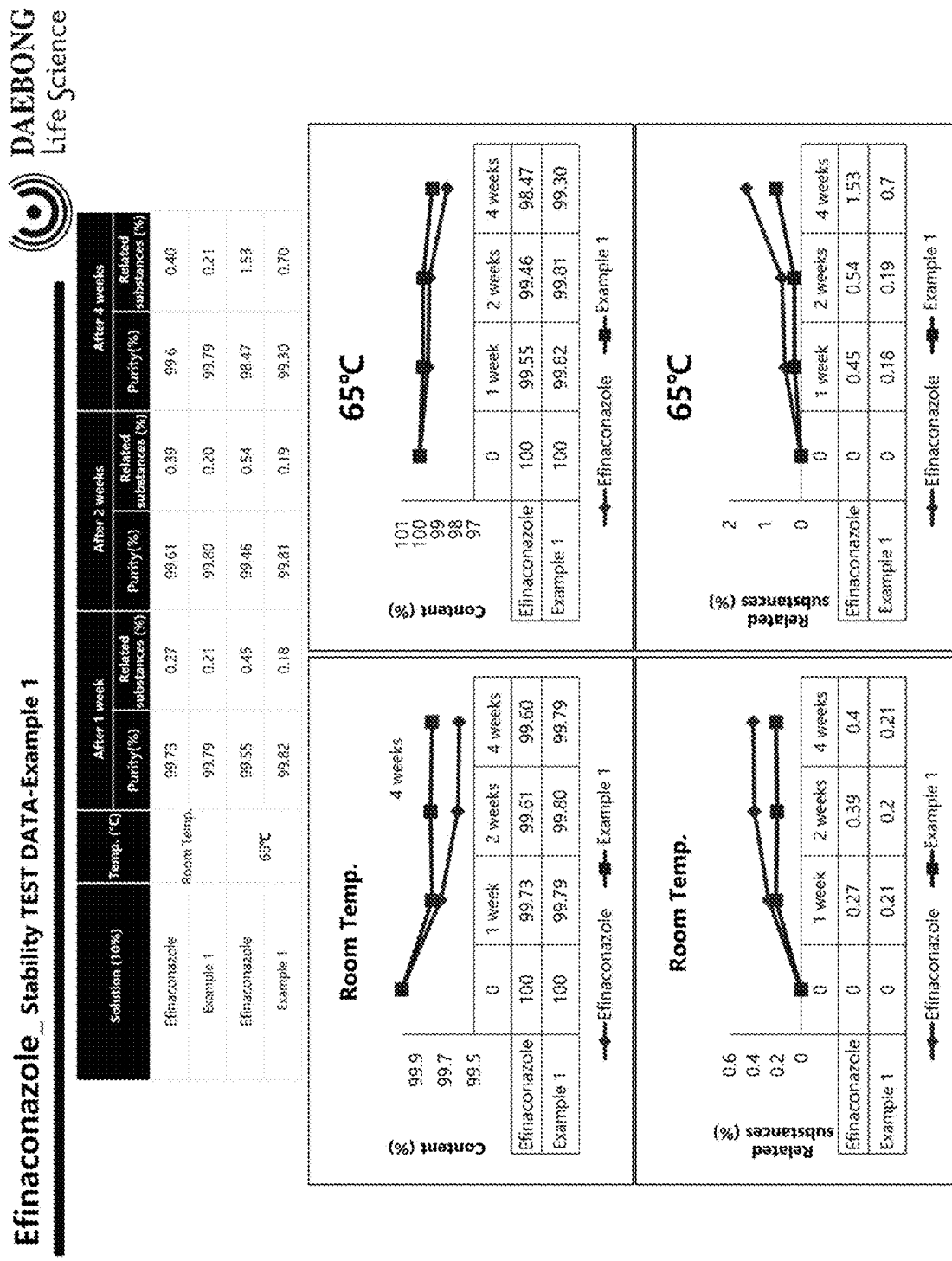
FIG. 7 shows graphs comparing the stability of a crystalline form of efinaconazole with that of a co-crystal of efinaconazole and polyethylene glycol.

As shown in FIG. 7, the co-crystal of efinaconazole according to the present invention has excellent stability to a solution and temperature, which was confirmed through comparative experiments.

The co-crystal of efinaconazole according to the present invention meets all requirements (that is, requirements in terms of chemical purity of the crystal and stability to a solution and temperature) for use as an active ingredient of the pharmaceutical composition.

A further aspect of the present invention is directed to a pharmaceutical composition for treating onychomycosis which includes the co-crystallization product of efinaconazole as an active pharmaceutical ingredient (API) and can be pharmaceutically formulated.

The pharmaceutical composition of the present invention may further include one or more excipients, in addition to the co-crystal of efinaconazole as an active ingredient. Examples of the excipients include carriers, adjuvants, and diluents. The pharmaceutical composition of the present invention is formulated into general pharmaceutical preparations for oral or parenteral administration by suitable techniques known in the art.

Particularly, the co-crystalline form of efinaconazole is a new solid drug that can be stably administered orally rather than an agent that is used by external application. Thus, the co-crystalline form of efinaconazole is considered very useful as an optimal pharmaceutical raw material whose utilization can be maximized.

Another aspect of the present invention is directed to a method for preparing the co-crystal of efinaconazole.

The co-crystal of efinaconazole can be prepared in an easy way. A detailed description of the method is given in the following.

First, at least one acceptable coformer selected from polyethylene glycol, nicotinamide, fumaric acid, hydroquinone, malonic acid, and caffeic acid is dissolved in an organic solvent to prepare a mixed solution.

The organic solvent may be selected from methanol, ethanol, isopropyl alcohol, n-propanol, isoamyl alcohol, acetone, ethyl methyl ketone, methyl isobutyl ketone, ethyl acetate, n-propyl acetate, n-butyl acetate, t-butyl acetate, toluene, dichloromethane, acetonitrile, and mixtures thereof. The organic solvent is preferably selected from dichloromethane, acetonitrile, methanol, and mixtures thereof.

The order of addition of the efinaconazole and the co-crystal forming agent to the organic solvent is not particularly limited. The efinaconazole and the coformer are dissolved with sufficient stirring. If needed, the efinaconazole and the coformer are dissolved under heating. It is preferable to completely dissolve the efinaconazole and the coformer.

Yet another aspect of the present invention is directed to a co-amorphous product of efinaconazole and a pharmaceutically acceptable coformer forming a co-amorphous phase.

The coformer may be selected from citric acid, oxalic acid, and a mixture thereof.

Generally, amorphous forms have higher solubility and bioavailability but lower stability than crystalline forms. Surprisingly, the co-amorphous product is highly stable and bioavailable compared to the crystalline form of pure efinaconazole, which will be more fully understood with reference to the following examples.

The present invention will be more specifically explained with reference to the following examples. However, it is to be noted that these examples are not intended to limit the scope of the invention.

EXAMPLES

Example 1—Preparation of Co-Crystal of Efinaconazole and Polyethylene Glycol (1:1 Ratio)

Efinaconazole (1 g) was dissolved in acetonitrile (5 mL) with stirring at room temperature. Polyethylene glycol-6000 (1 g) was added to the solution, followed by stirring for 1 h. The solvent was distilled off under reduced pressure. Spontaneous formation of a co-crystal of efinaconazole and polyethylene glycol-6000 was observed within a short time. After drying under vacuum, the crystal was recovered in a yield of 95%. The purity of the crystal was 99.5%. A powder X-ray diffraction (XRD) spectrum and a differential scanning calorimetry thermogram of the co-crystal of efinaconazole and polyethylene glycol-6000 are shown in FIGS. 1 and 3, respectively.

Example 2—Preparation of Co-Crystal of Efinaconazole and Caffeic Acid (1:1 Ratio)

Efinaconazole (1 g) was dissolved in methanol (5 mL) with stirring at room temperature. Caffeic acid (1 g) was added to the solution, followed by stirring for 1 h. The solvent was distilled off under reduced pressure. Spontaneous formation of a co-crystal of efinaconazole and caffeic acid was observed within a short time. After drying under vacuum, the crystal was recovered in a yield of 92%. The purity of the crystal was 99.5%.

A powder X-ray diffraction (XRD) spectrum and a differential scanning calorimetry thermogram of the co-crystal of efinaconazole and caffeic acid are shown in FIGS. 2 and 4, respectively.

Example 3—Preparation of Co-Crystal of Efinaconazole and Nicotinamide (1:1 Ratio)

Efinaconazole (1 g) was dissolved in acetonitrile (5 mL) with stirring at room temperature. Nicotinamide (1 g) was added to the solution, followed by stirring for 1 h. The solvent was distilled off under reduced pressure. Spontaneous formation of a co-crystal of efinaconazole and nicotinamide was observed within a short time. After drying under vacuum, the crystal was recovered in a yield of 95%.

Figure 8:
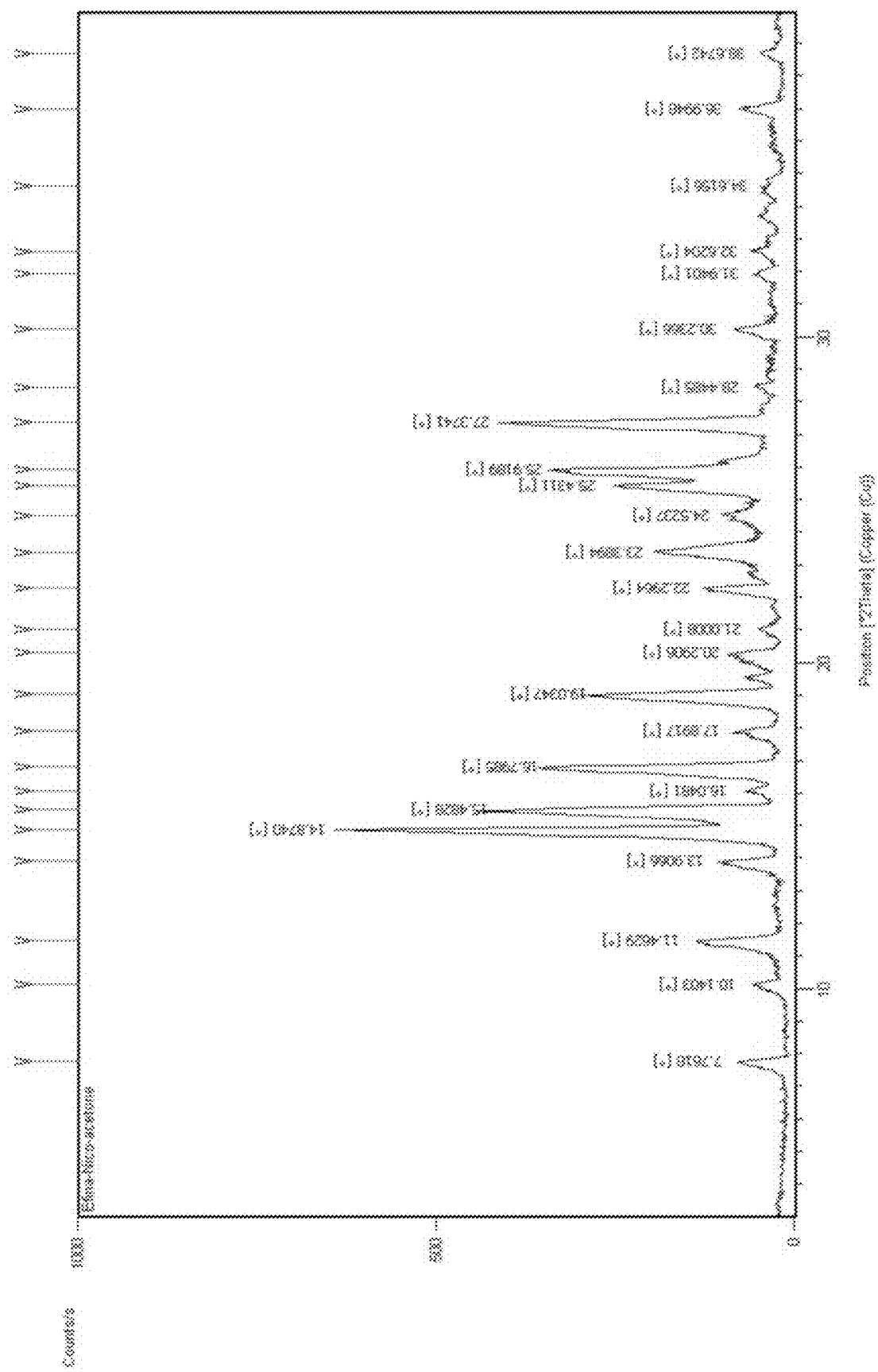
FIG. 8 is a powder XRD pattern of a co-crystal of efinaconazole and nicotinamide.
Figure 9:
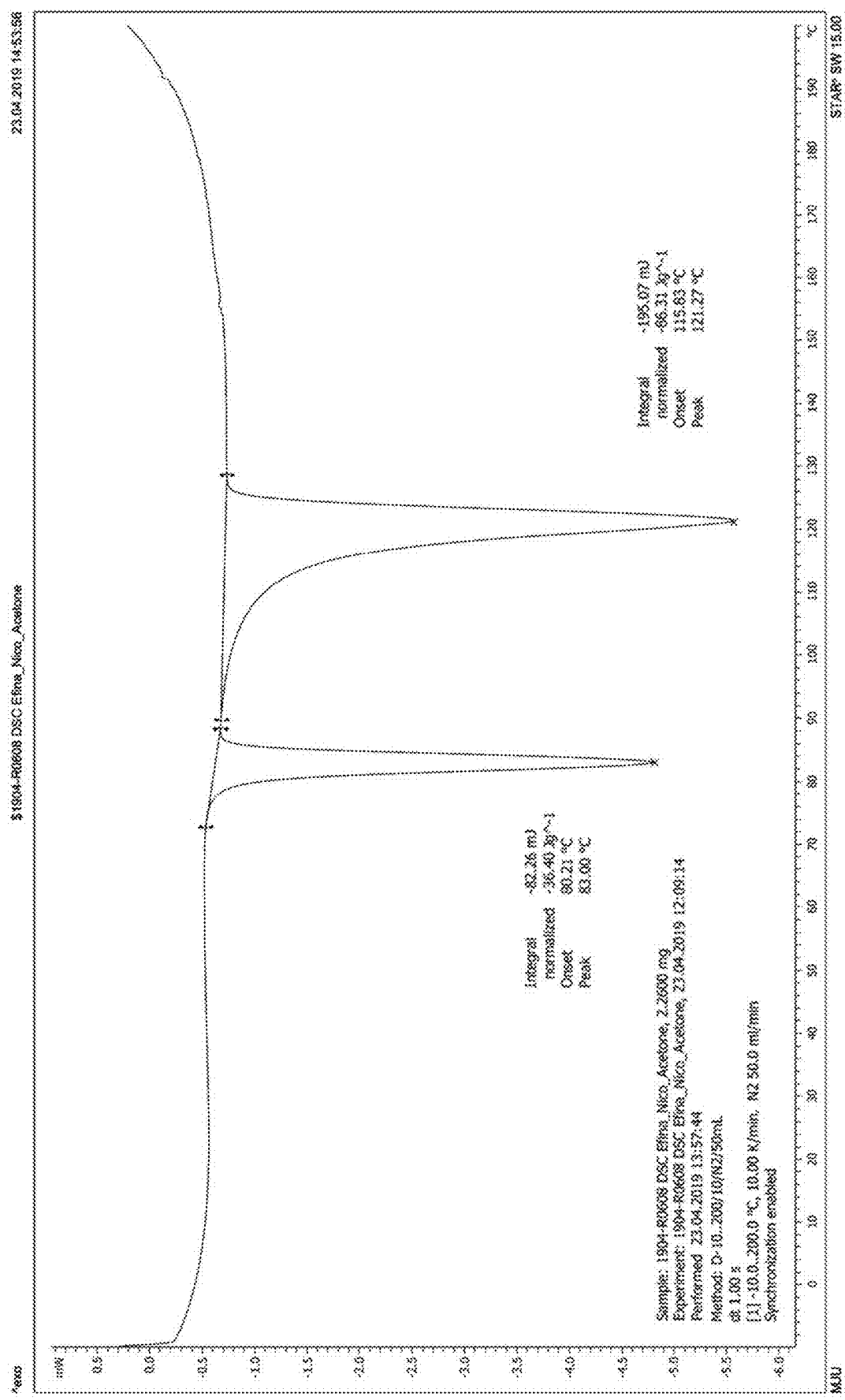
FIG. 9 is a DSC thermogram of a co-crystal of efinaconazole and nicotinamide.

A powder X-ray diffraction (XRD) spectrum and a differential scanning calorimetry thermogram of the co-crystal of efinaconazole and nicotinamide are shown in FIGS. 8 and 9, respectively.

Example 4—Preparation of Co-Crystal of Efinaconazole and Fumaric Acid (3:1 Ratio)

Efinaconazole (0.9 g) was dissolved in tetrahydrofuran (7.2 mL) with stirring at room temperature. Fumaric acid (0.3 g) was added to the solution, followed by stirring for 1 h. The solvent was distilled off under reduced pressure. Spontaneous formation of a co-crystal of efinaconazole and fumaric acid was observed within a short time. After drying under vacuum, the crystal was recovered in a yield of 90%.

Figure 10:
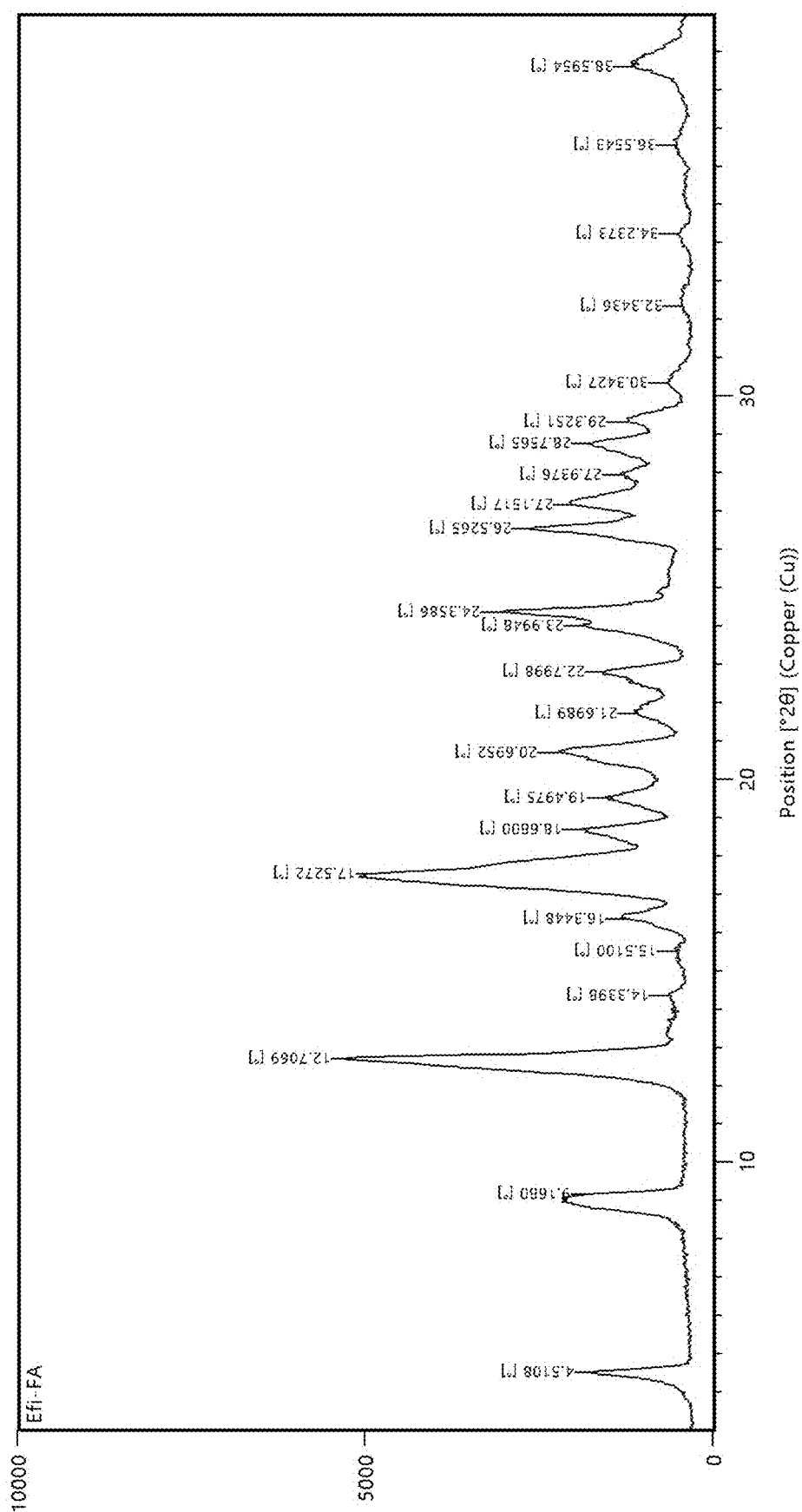
FIG. 10 is a powder XRD pattern of a co-crystal of efinaconazole and fumaric acid.
Figure 11:
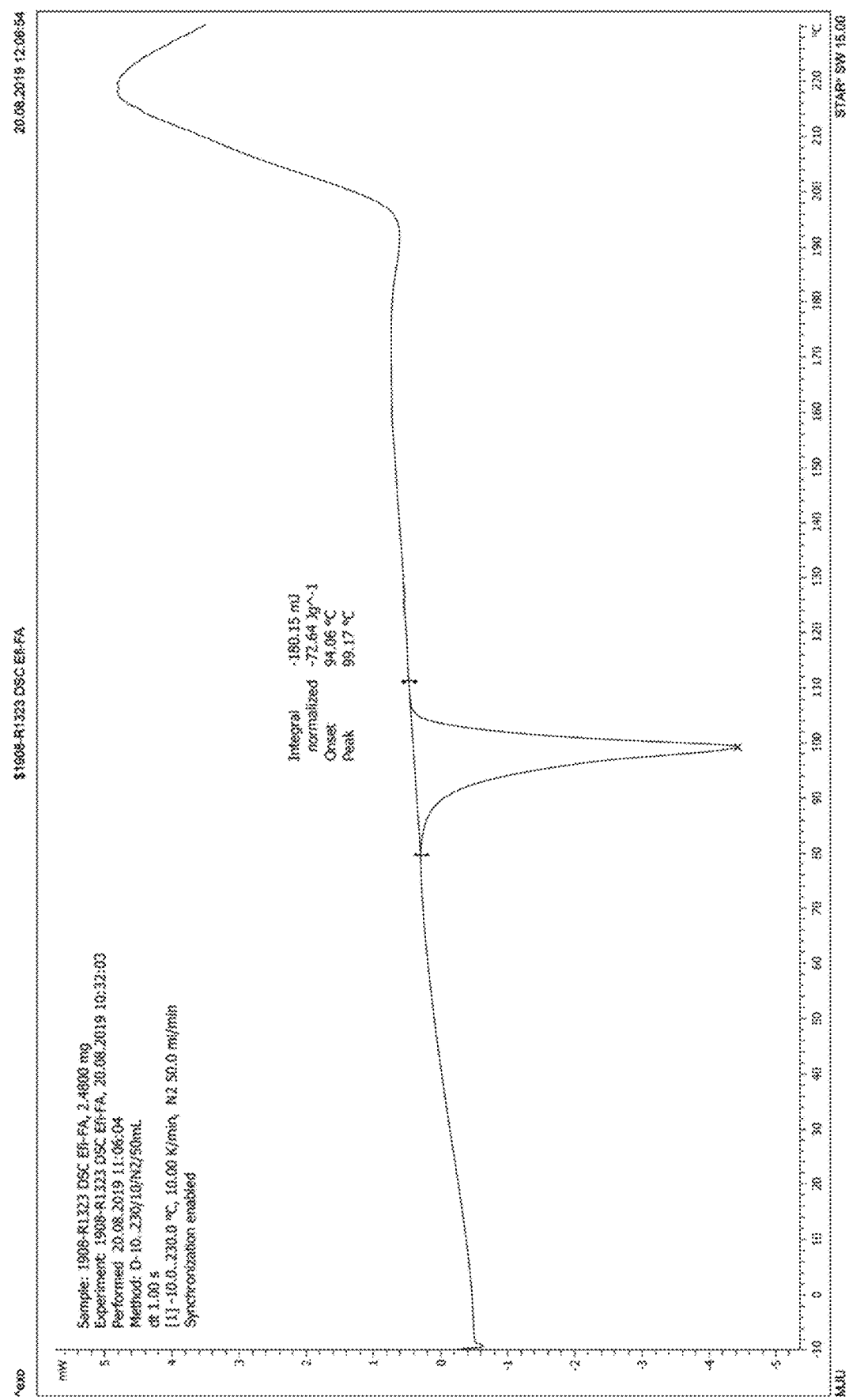
FIG. 11 is a DSC thermogram of a co-crystal of efinaconazole and fumaric acid.

A powder X-ray diffraction (XRD) spectrum and a differential scanning calorimetry thermogram of the co-crystal of efinaconazole and fumaric acid are shown in FIGS. 10 and 11, respectively.

Example 5—Preparation of Co-Crystal of Efinaconazole and Hydroquinone (1:1 Ratio)

Figure 12:
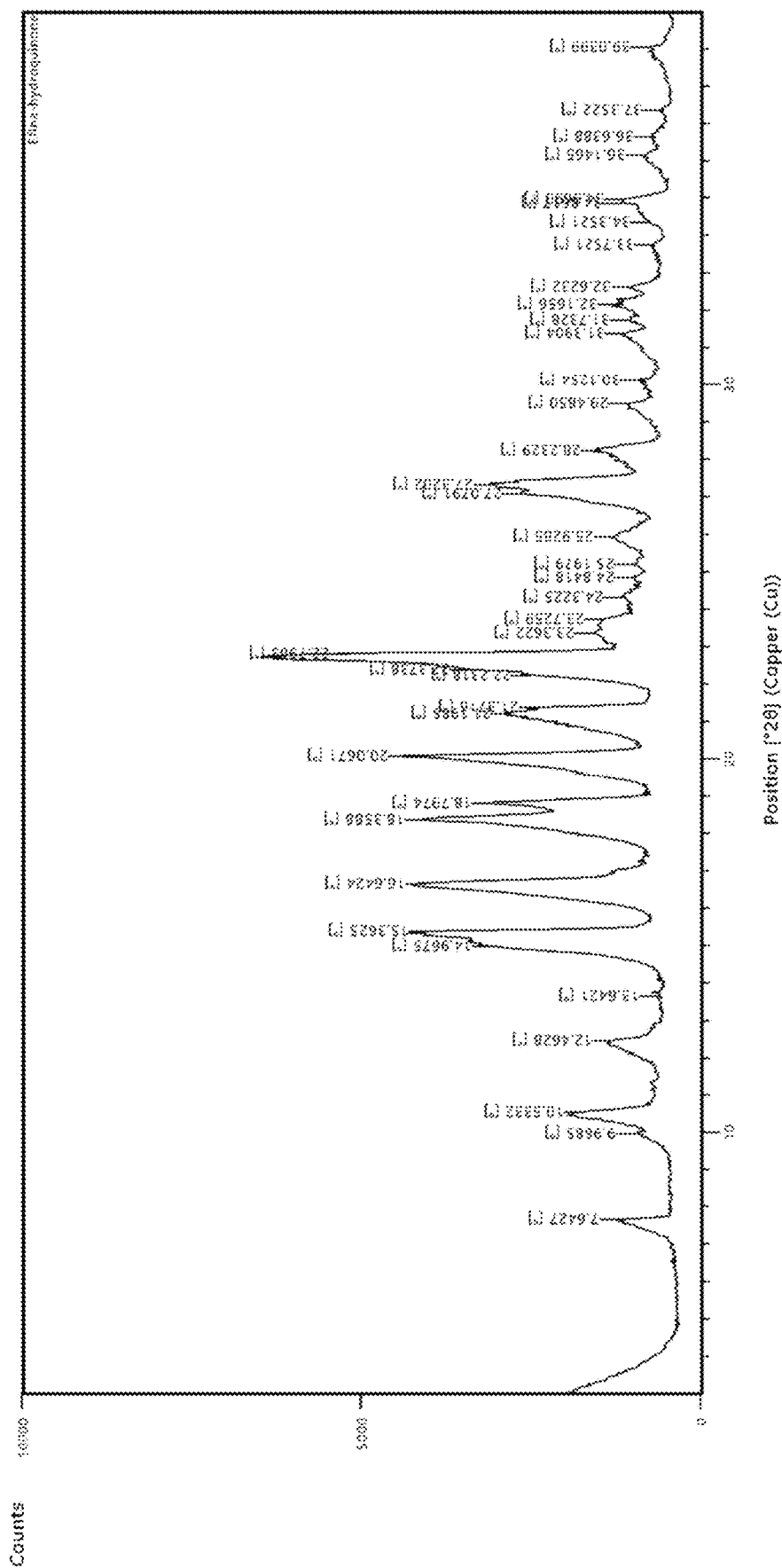
FIG. 12 is a powder XRD pattern of a co-crystal of efinaconazole and hydroquinone.
Figure 13:
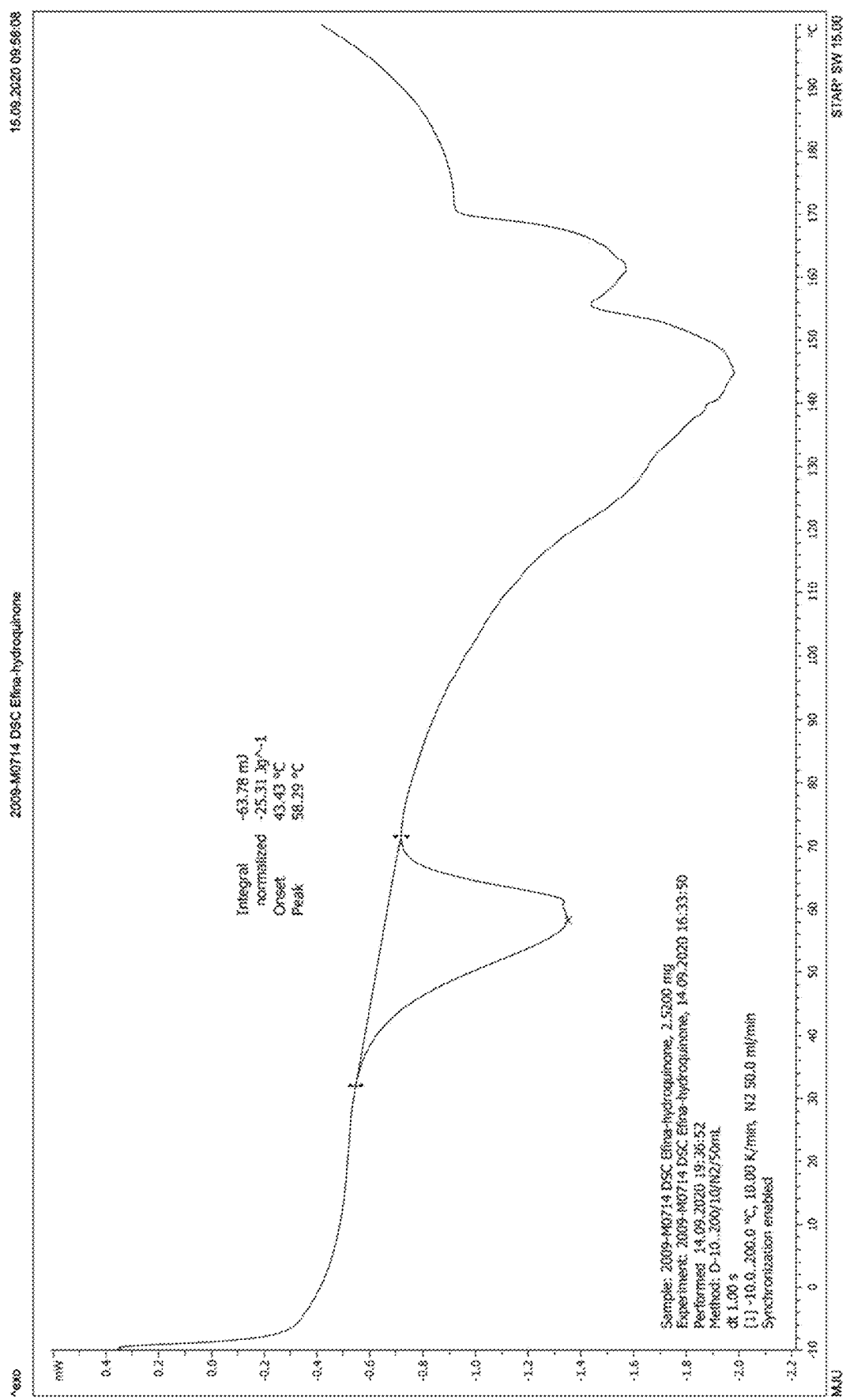
FIG. 13 is a DSC thermogram of a co-crystal of efinaconazole and hydroquinone.

Efinaconazole (1 g) was dissolved in methanol (5 mL) with stirring at room temperature. Hydroquinone (1 g) was added to the solution, followed by stirring for 1 h. The solvent was distilled off under reduced pressure. Spontaneous formation of a co-crystal of efinaconazole and hydroquinone was observed within a short time. After drying under vacuum, the crystal was recovered in a yield of 90%. A powder X-ray diffraction (XRD) spectrum and a differential scanning calorimetry thermogram of the co-crystal of efinaconazole and hydroquinone are shown in FIGS. 12 and 13, respectively. The XRD data of the co-crystal were different from those of efinaconazole and the DSC thermogram of the co-crystal had a maximum endothermic peak at 58.29° C., indicating that the co-crystal is a novel material having different physicochemical properties from efinaconazole.

Example 6—Preparation of Co-Amorphous Form of Efinaconazole and Citric Acid (1:1 Ratio)

Figure 14:
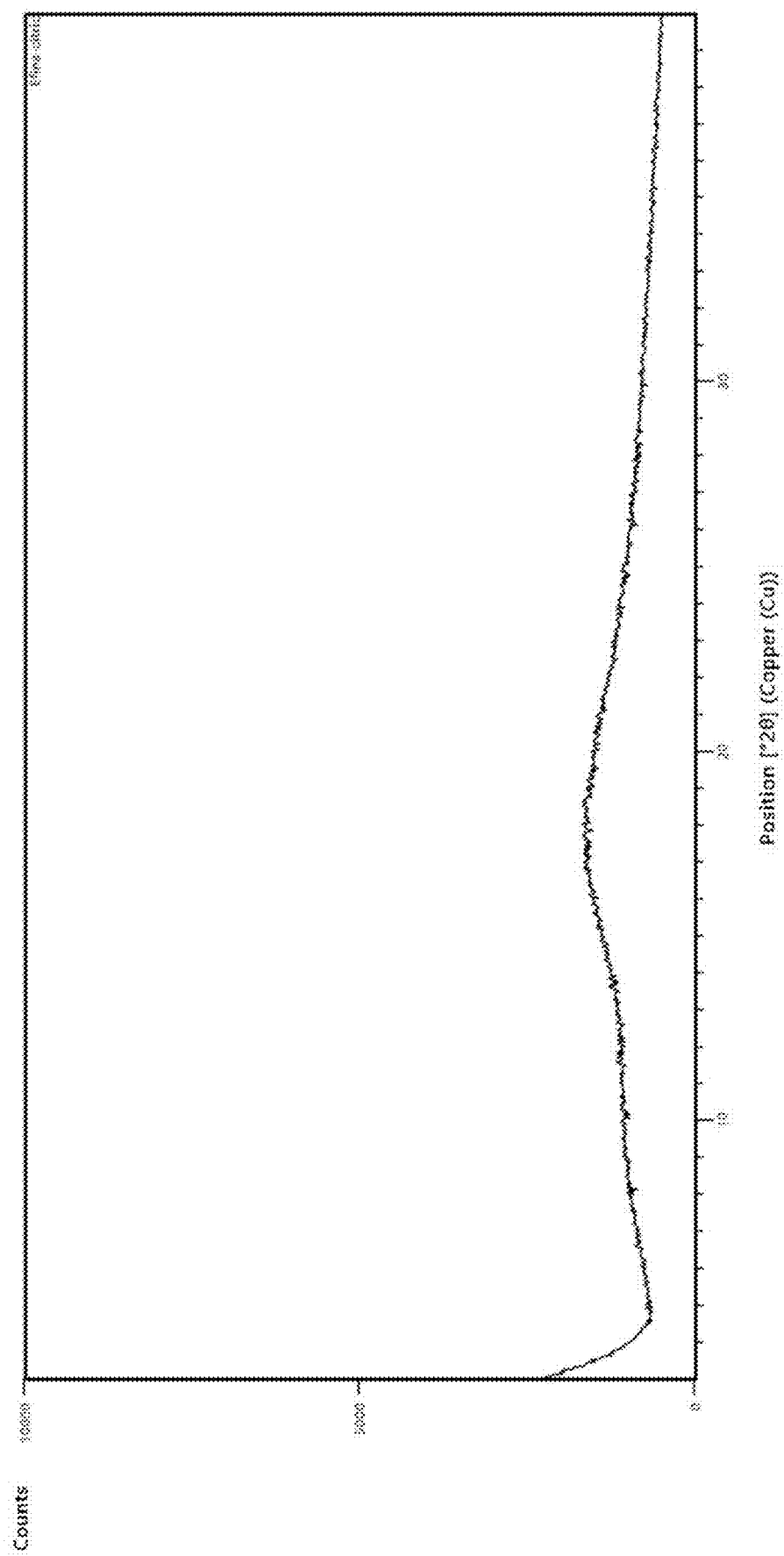
FIG. 14 is a powder XRD pattern of a co-amorphous form of efinaconazole and citric acid.
Figure 15:
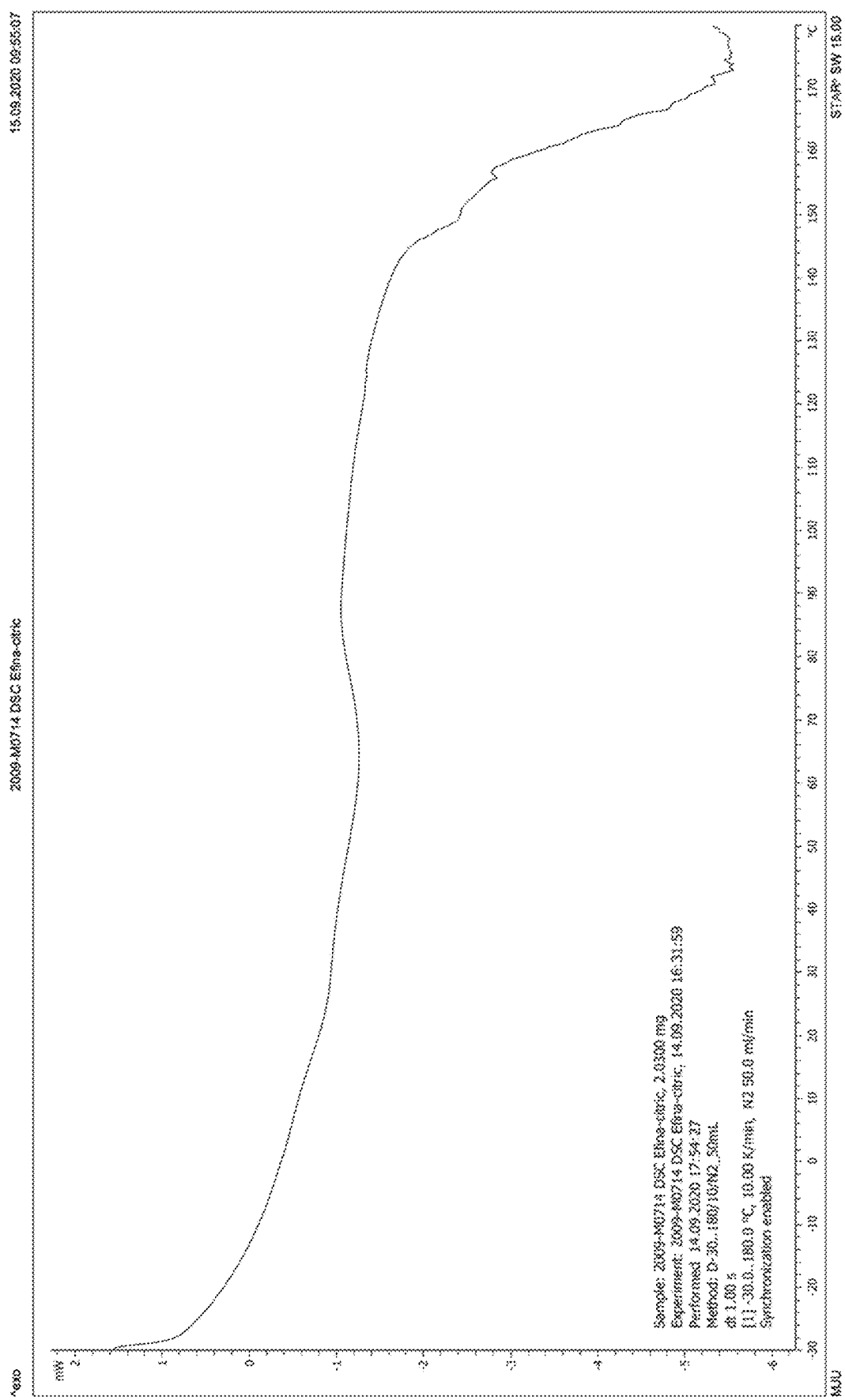
FIG. 15 is a DSC thermogram of a co-amorphous form of efinaconazole and citric acid.

Efinaconazole (1 g) was dissolved in methanol (5 mL) with stirring at room temperature. Citric acid (1 g) was added to the solution, followed by stirring for 1 h. The solvent was distilled off under reduced pressure. Spontaneous formation of a co-amorphous form of efinaconazole and citric acid was observed within a short time. After drying under vacuum, the co-amorphous form was recovered in a yield of 97%. A powder X-ray diffraction (XRD) spectrum and a differential scanning calorimetry thermogram of the co-amorphous form of efinaconazole and citric acid are shown in FIGS. 14 and 15, respectively. The XRD data of the co-amorphous form were different from those of efinaconazole and no diffraction angle (2θ) and maximum endothermic peak were observed, demonstrating that the product was amorphous. These results indicate that the product is a novel material having different physicochemical properties from efinaconazole.

Example 7—Preparation of Co-Amorphous Form of Efinaconazole and Oxalic Acid (1:1 Ratio)

Figure 16:
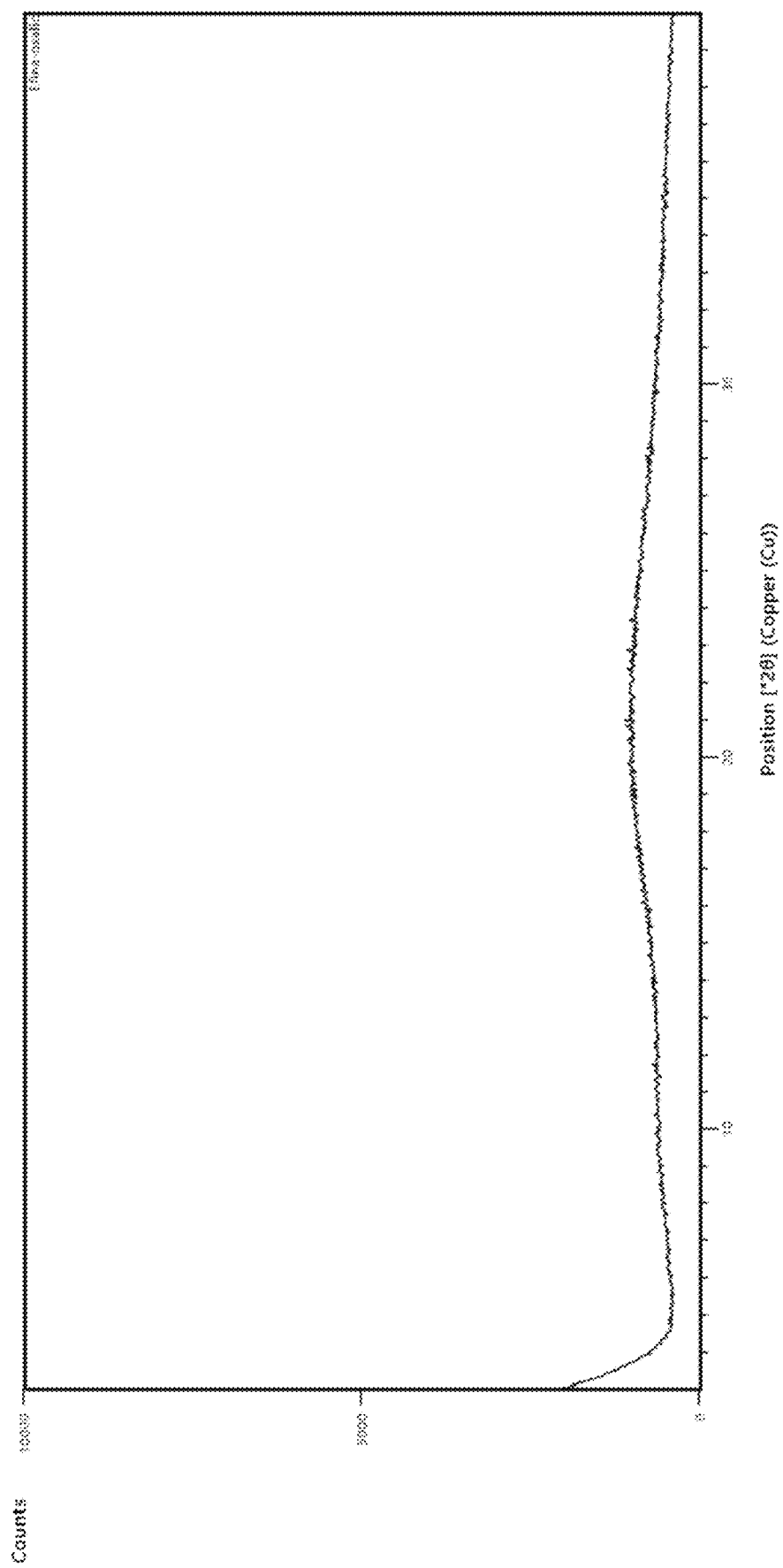
FIG. 16 is a powder XRD pattern of a co-amorphous form of efinaconazole and oxalic acid.
Figure 17:
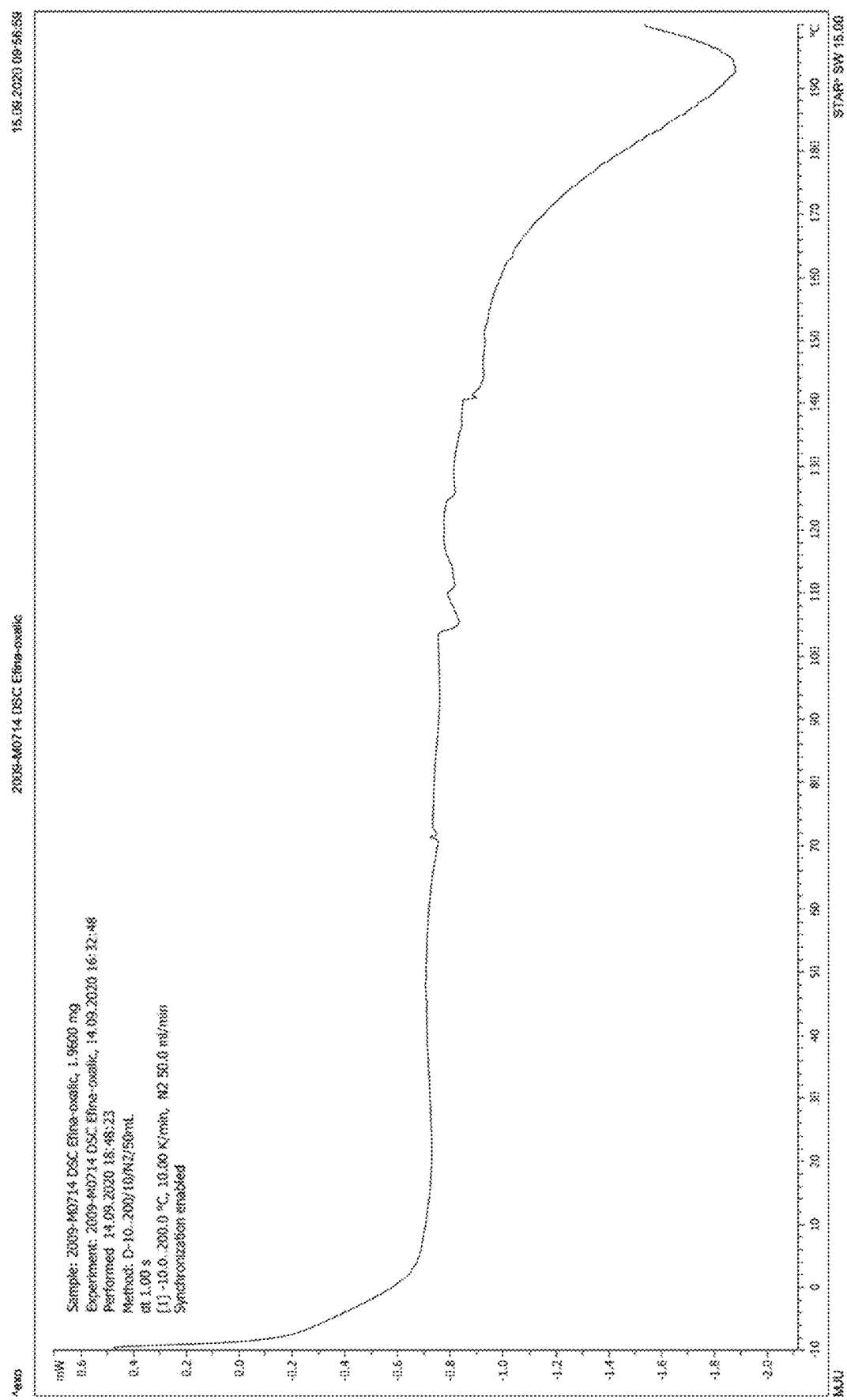
FIG. 17 is a DSC thermogram of a co-amorphous form of efinaconazole and oxalic acid.

Efinaconazole (1 g) was dissolved in methanol (5 mL) with stirring at room temperature. Oxalic acid (1 g) was added to the solution, followed by stirring for 1 h. The solvent was distilled off under reduced pressure. Spontaneous formation of a co-amorphous form of efinaconazole and oxalic acid was observed within a short time. After drying under vacuum, the co-amorphous form was recovered in a yield of 92%. A powder X-ray diffraction (XRD) spectrum and a differential scanning calorimetry thermogram of the co-amorphous form of efinaconazole and oxalic acid are shown in FIGS. 16 and 17, respectively. The XRD data of the co-amorphous form were different from those of efinaconazole and no diffraction angle (2θ) and maximum endothermic peak were observed, demonstrating that the product was amorphous. These results indicate that the product is a novel material having different physicochemical properties from efinaconazole.

Example 8—Preparation of Co-Crystal of Efinaconazole and Malonic Acid (1:1 Ratio)

Figure 18:
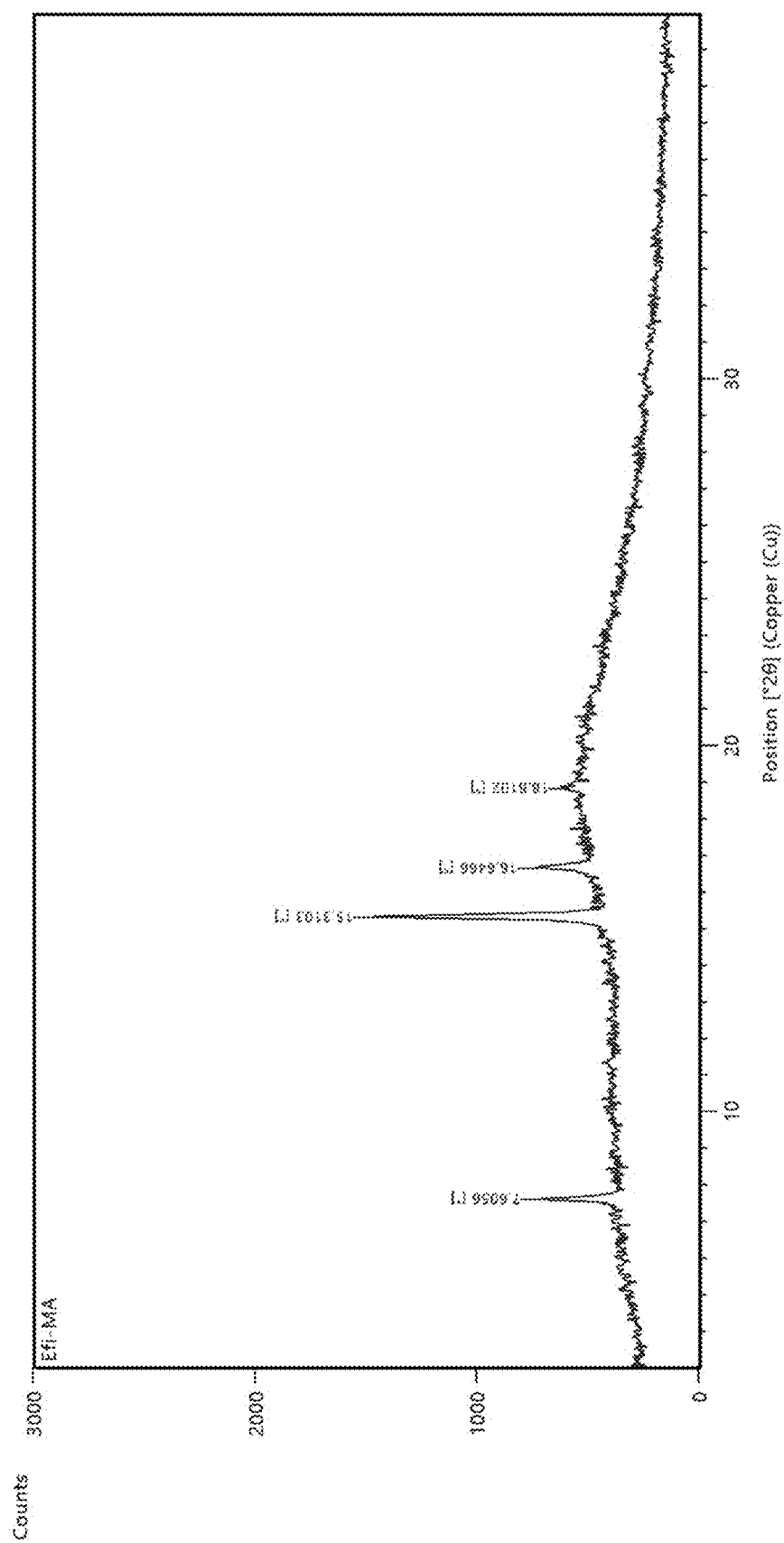
FIG. 18 is a powder XRD pattern of a co-crystal of efinaconazole and malonic acid.
Figure 19:
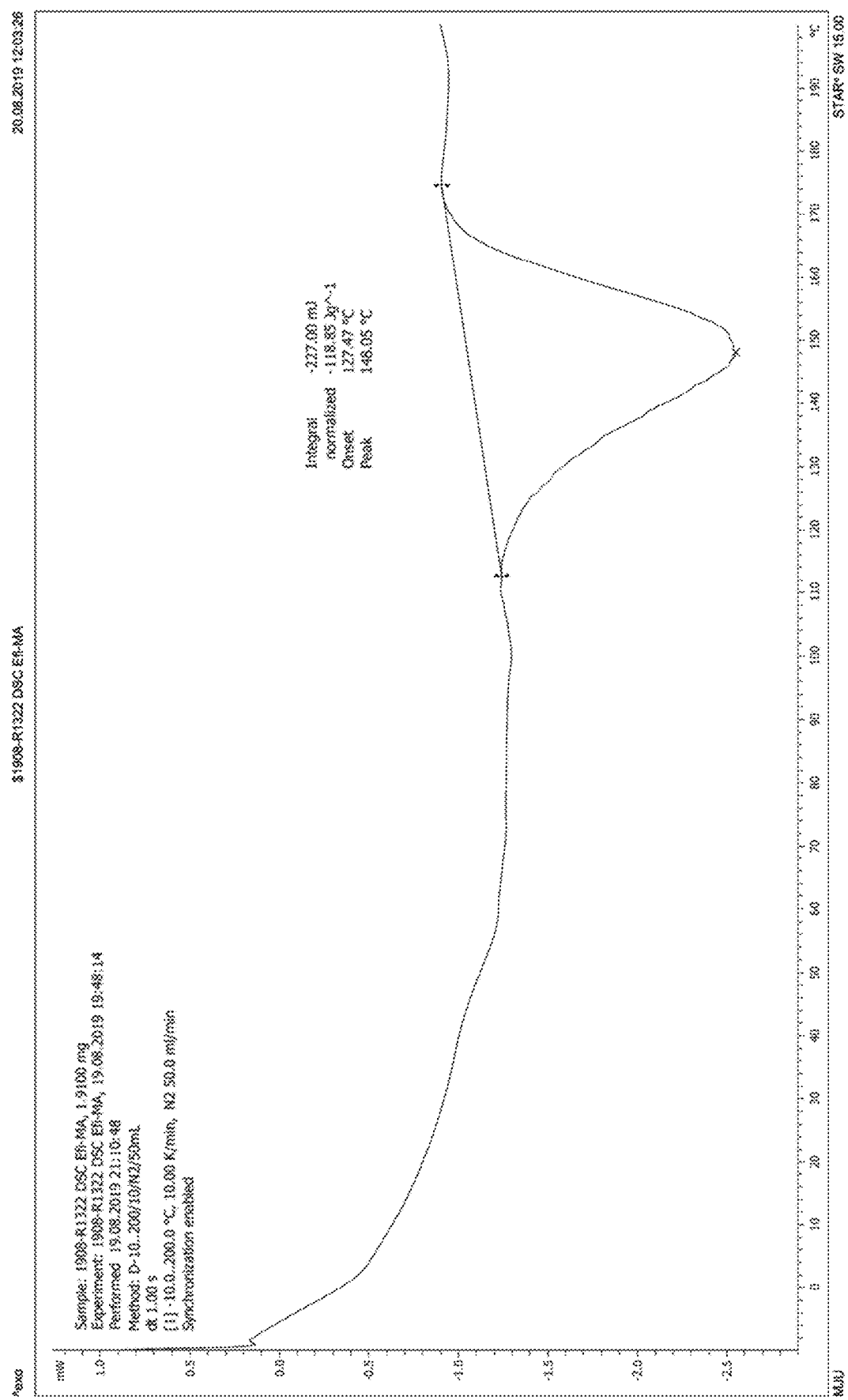
FIG. 19 is a DSC thermogram of a co-crystal of efinaconazole and malonic acid.
Figure 20:
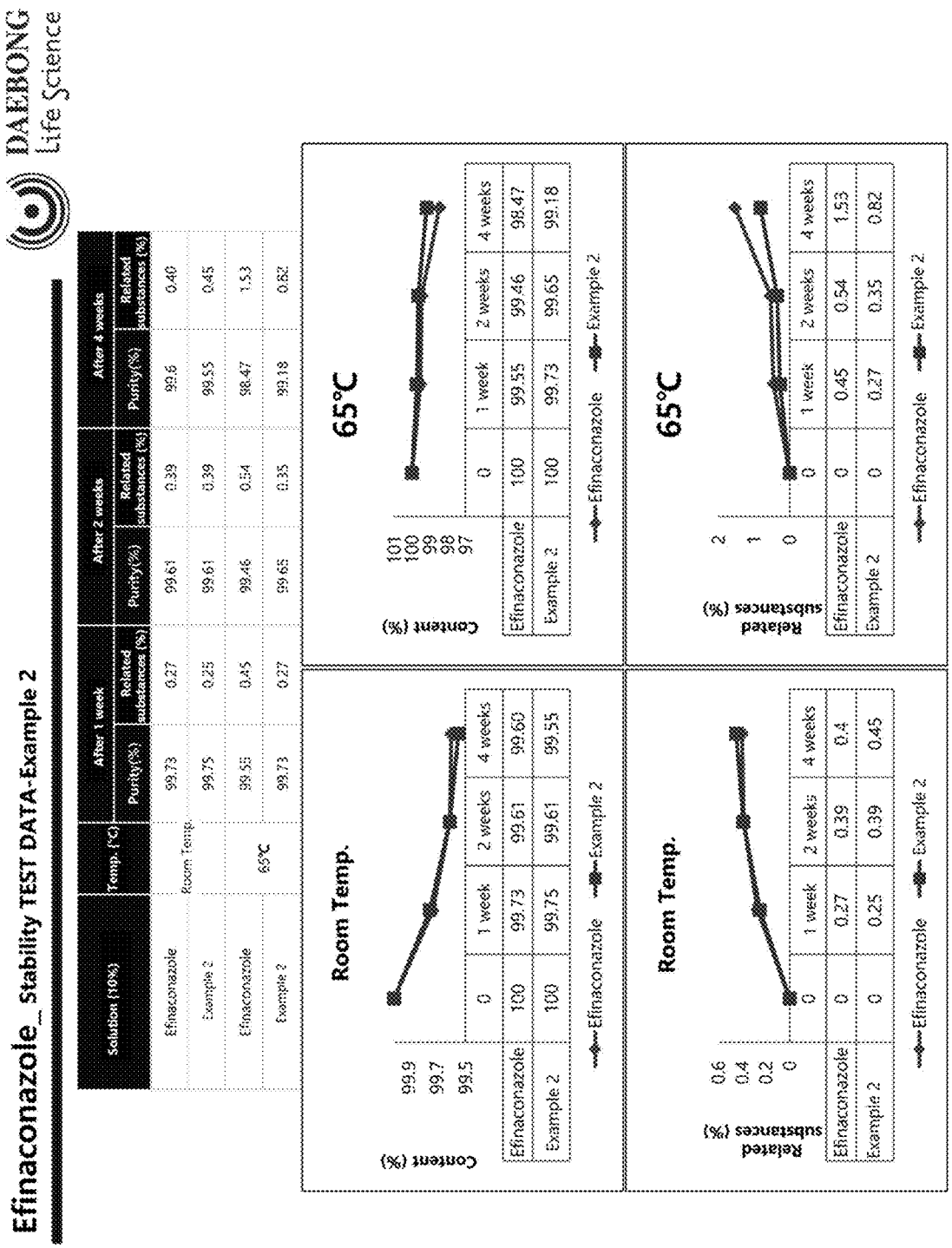
FIG. 20 shows graphs comparing the stability of a crystalline form of efinaconazole with that of a co-crystal of efinaconazole and caffeic acid.
Figure 21:
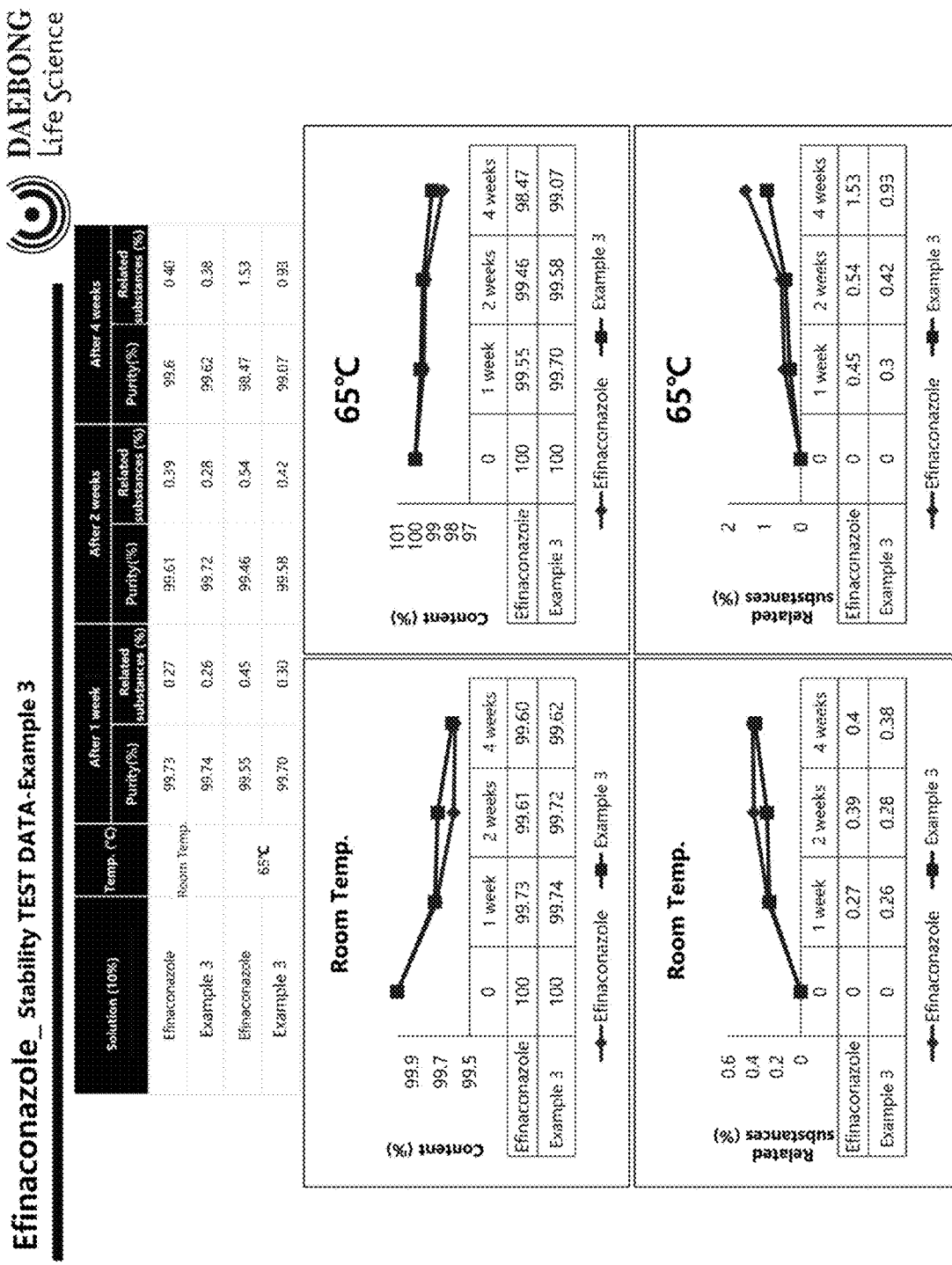
FIG. 21 shows graphs comparing the stability of a crystalline form of efinaconazole with that of a co-crystal of efinaconazole and nicotinamide.
Figure 22:
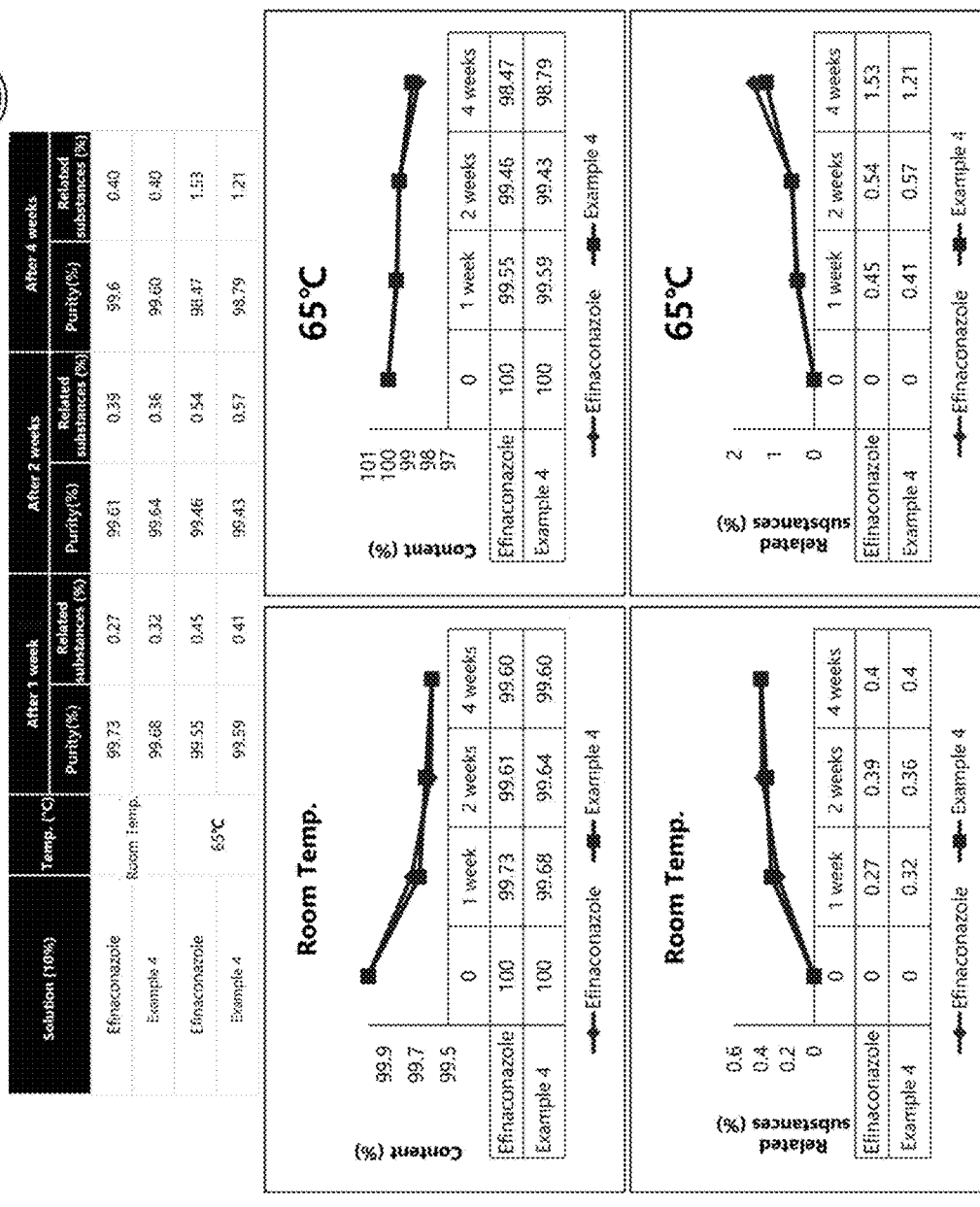
FIG. 22 shows graphs comparing the stability of a crystalline form of efinaconazole with that of a co-crystal of efinaconazole and fumaric acid.
Figure 23:
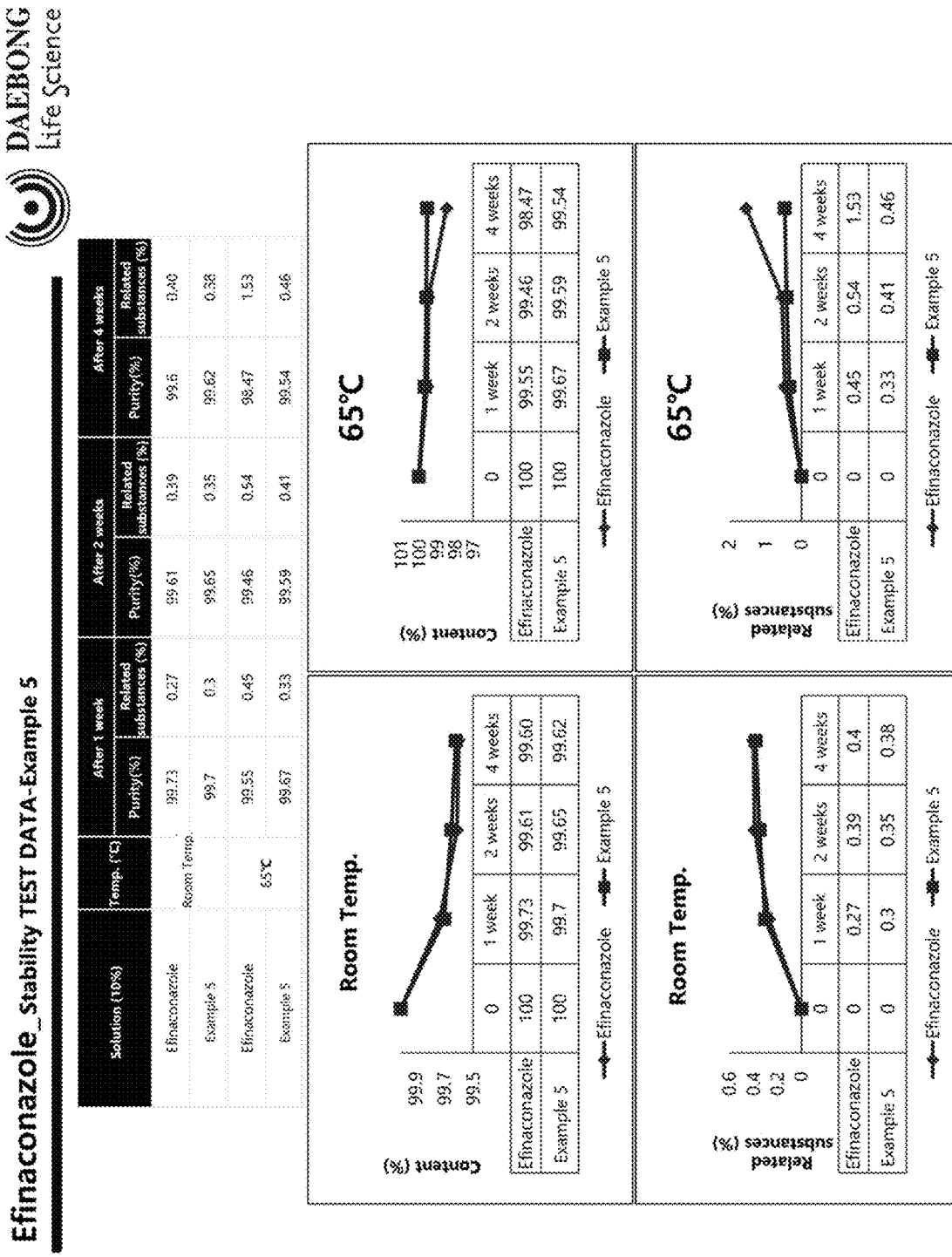
FIG. 23 shows graphs comparing the stability of a crystalline form of efinaconazole with that of a co-crystal of efinaconazole and hydroquinone.
Figure 24:
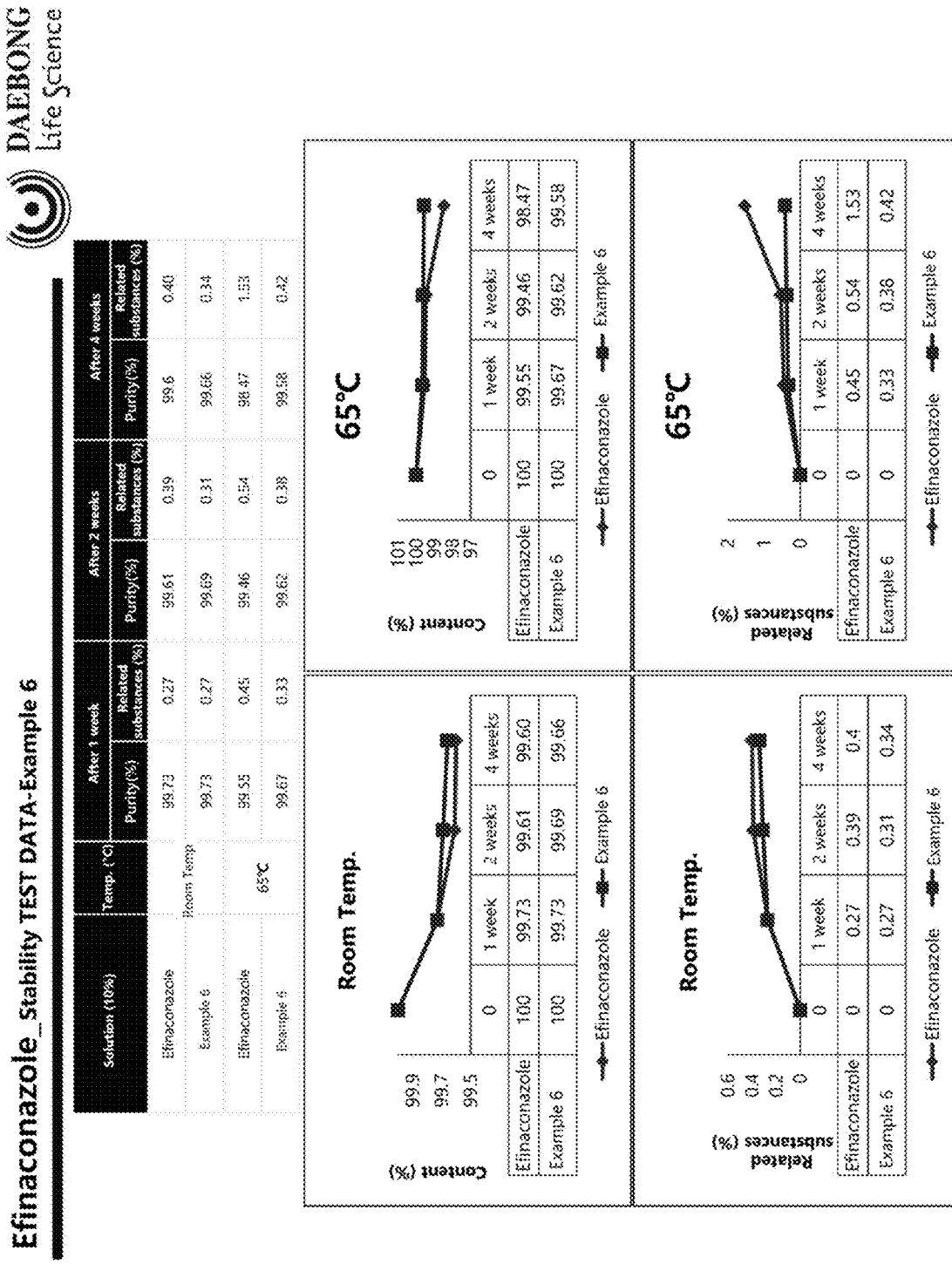
FIG. 24 shows graphs comparing the stability of a co-amorphous form of efinaconazole with that of a co-crystal of efinaconazole and citric acid.
Figure 25:
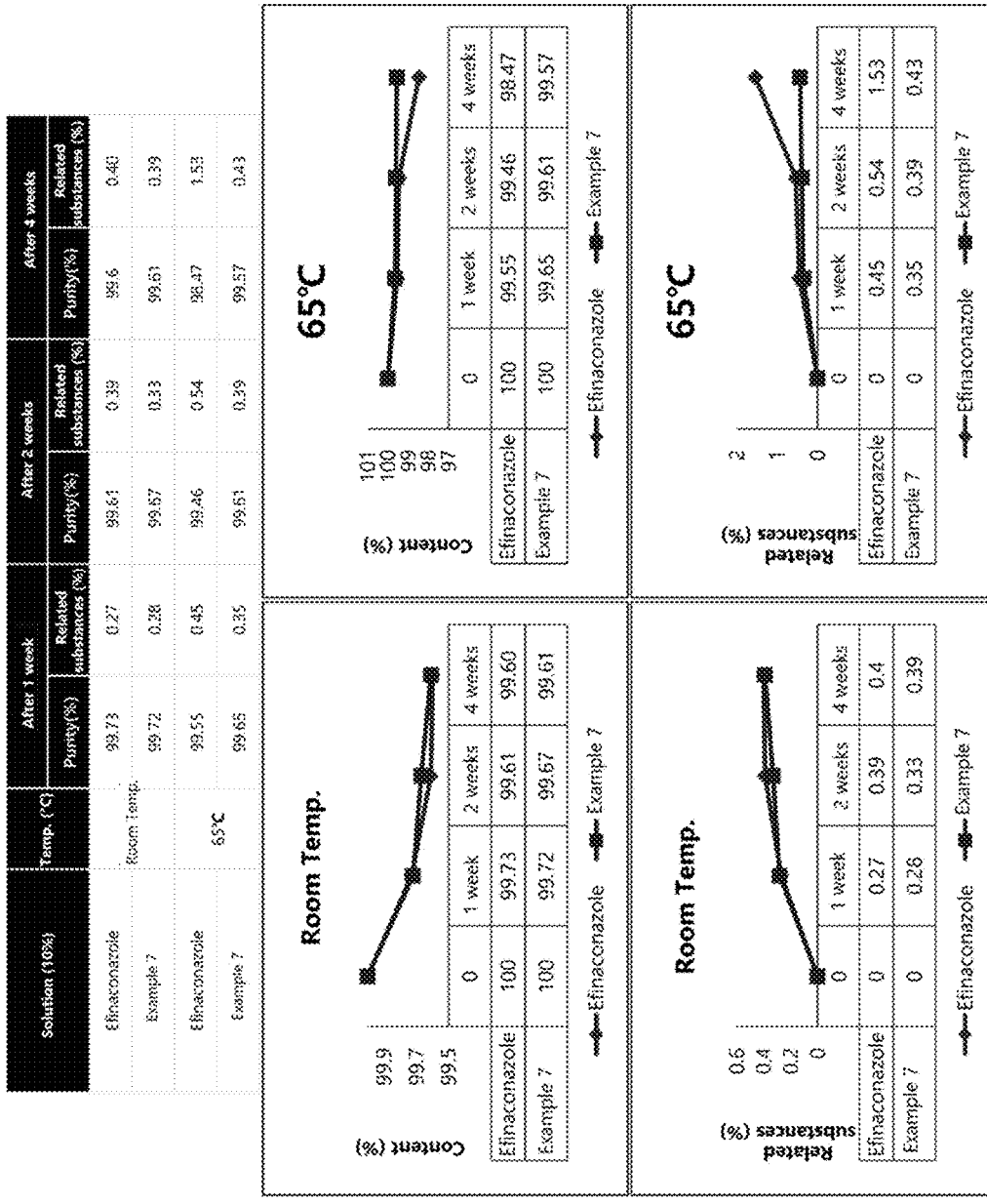
FIG. 25 shows graphs comparing the stability of a co-amorphous form of efinaconazole with that of a co-crystal of efinaconazole and oxalic acid.
Figure 26:
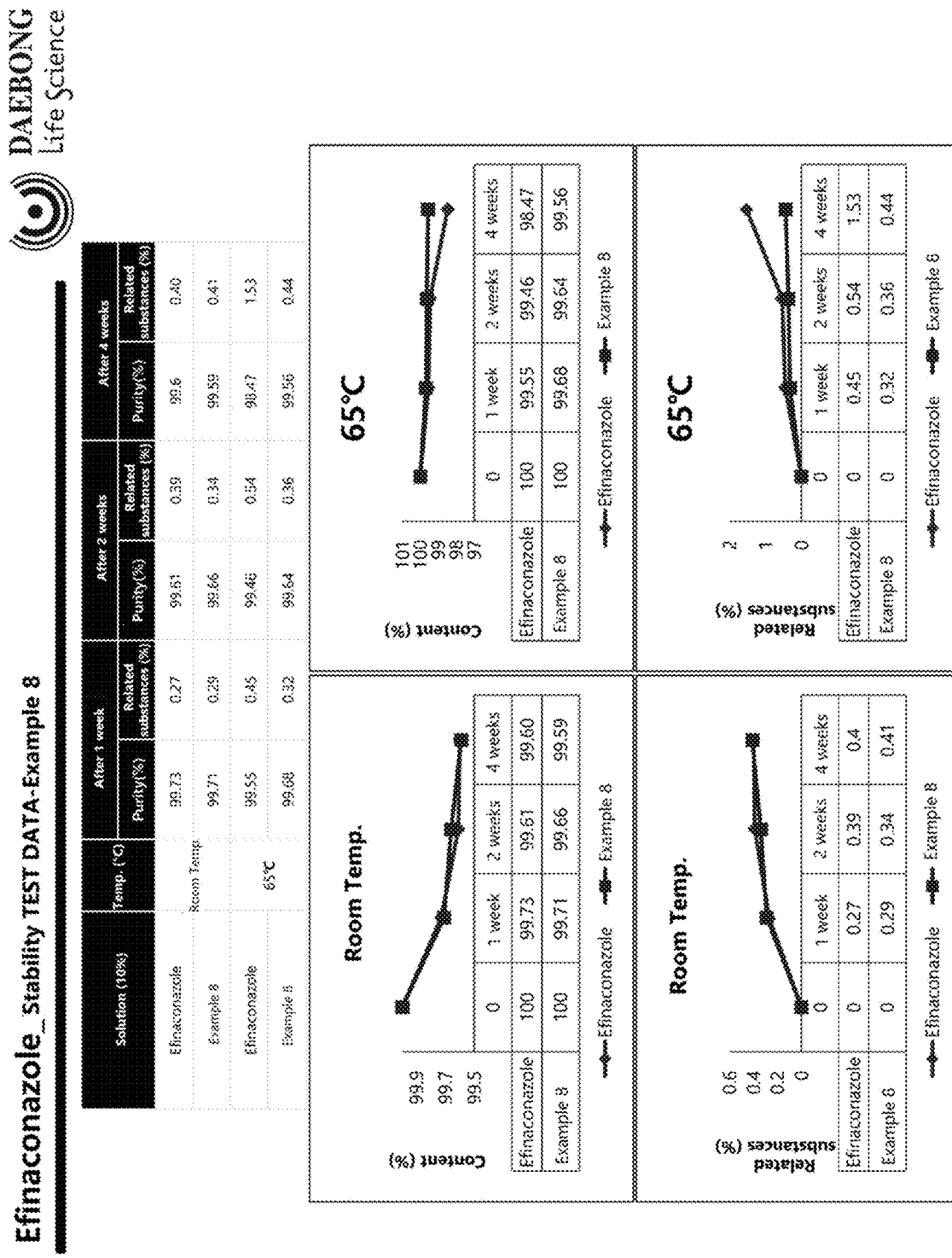
FIG. 26 shows graphs comparing the stability of a crystalline form of efinaconazole with that of a co-crystal of efinaconazole and malonic acid.

Efinaconazole (1 g) was dissolved in methanol (5 mL) with stirring at room temperature. Malonic acid (1 g) was added to the solution, followed by stirring for 1 h. The solvent was distilled off under reduced pressure. Spontaneous formation of a co-crystal of efinaconazole and malonic acid was observed within a short time. After drying under vacuum, the crystal was recovered in a yield of 90%. A powder X-ray diffraction (XRD) spectrum and a differential scanning calorimetry thermogram of the co-crystal of efinaconazole and malonic acid are shown in FIGS. 18 and 19, respectively. The XRD data of the co-crystal were different from those of efinaconazole and the DSC thermogram of the co-crystal had a maximum endothermic peak at 148.05° C., indicating that the co-crystal is a novel material having different physicochemical properties from efinaconazole.

TEST EXAMPLES

[Stability Test]

The stabilities of the co-crystals of efinaconazole to temperature and a solution were evaluated and compared by the following experimental method.

*Experimental Method

After the co-crystalline form of efinaconazole prepared in Example 1 was dissolved in a solution and allowed to stand at different temperatures (at room temperature and in an oven at 65° C.) for different periods of time (1 week, 2 weeks, and 4 weeks), its purities were determined by high-performance liquid chromatography (HPLC).

The results are shown in Table 1 and FIG. 7.

TABLE 1

| Solution (10%) | Temp. (° C.) | After 1 week | | After 2 weeks | | After 4 weeks | |
|---|---|---|---|---|---|---|---|
| | | HPLC (%) | Related substances (%) | HPLC (%) | Related substances (%) | HPLC (%) | Related substances (%) |
| Efinaconazole | Room temp. | 99.73 | 0.27 | 99.61 | 0.39 | 99.60 | 0.40 |
| Example 1 | | 99.79 | 0.21 | 99.80 | 0.20 | 99.79 | 0.21 |

TABLE 1-continued

| Solution (10%) | Temp. (° C.) | After 1 week | | After 2 weeks | | After 4 weeks | |
|---|---|---|---|---|---|---|---|
| | | HPLC (%) | Related substances (%) | HPLC (%) | Related substances (%) | HPLC (%) | Related substances (%) |
| Efinaconazole | 65 | 99.55 | 0.45 | 99.46 | 0.54 | 98.47 | 1.53 |
| Example 1 | | 99.80 | 0.18 | 99.81 | 0.19 | 99.30 | 0.70 |

As can be seen from the results in Table 1 and FIG. 7, the co-crystal of efinaconazole was more stable in the temperatures and the solution than efinaconazole, thus being more suitable for drug preparation. In addition, the co-crystal of efinaconazole is considered as a novel material that meets all requirements for use as an active ingredient of a pharmaceutical composition.

[Non-Clinical Trial]

For a non-clinical trial, the co-crystal of efinaconazole prepared in Example 1 was administered orally to 6 beagle dogs. As a result, a bioavailability as high as 36% was achieved even with a small dose (3 mg) of the co-crystal of efinaconazole and no adverse reactions were observed in the beagle dogs, demonstrating the safety of the co-crystal of efinaconazole.

For reference, the oral bioavailability of the co-crystal of efinaconazole was compared with those of other antifungals. The results are shown in Table 2. As can be seen from the results in Table 2, the bioavailability of the co-crystal of efinaconazole was higher than those of other antifungals, including itraconazole, despite the small dose of the co-crystal of efinaconazole. Therefore, oral administration of the co-crystal of efinaconazole is expected to be therapeutically very effective.

TABLE 2

| Triazole antifungal | Voriconazole | Itraconazole | Efinaconazole + Coformer |
|---|---|---|---|
| Routes of administration | Oral | Oral | Oral |
| Dose | 200 mg | 100 mg | 3 mg |
| Oral Bioavailability(%) | 96% | 55% | 36% |

The invention claimed is:

1. A co-crystallization product of efinaconazole and a pharmaceutically acceptable coformer forming a co-crystalline phase, wherein the coformer includes polyethylene glycol, nicotinamide, fumaric acid, or a mixture thereof.

2. The co-crystallization product of efinaconazole according to claim 1, wherein:
the coformer includes polyethylene glycol, and
the polyethylene glycol includes polyethylene glycol-6000.

3. The co-crystallization product of efinaconazole according to claim 1, wherein:
the coformer includes polyethylene glycol, and
a powder X-ray diffraction (XRD) spectrum of the co-crystallization product has peaks at diffraction angles (2θ) of 7.78°, 11.50°, 13.85°, 15.49°, 16.79°, 18.97°, 19.22°, 23.57°, 26.18°, and 27.09°.

4. The co-crystallization product of efinaconazole according to claim 3, wherein a differential scanning calorimetry (DSC) thermogram of the co-crystallization product has maximum endothermic peaks at 61.62° C. and 78.78° C.

5. An oral or parenteral pharmaceutical composition, the composition comprising, as an active ingredient, the co-crystallization product of efinaconazole according to claim 1.

6. A method for preparing a co-crystallization product of efinaconazole, the method comprising dissolving efinaconazole and a pharmaceutically acceptable coformer in an organic solvent to prepare a mixed solution and evaporating the mixed solution to remove the solvent,
wherein the coformer includes polyethylene glycol, nicotinamide, fumaric acid, or a mixture thereof.

7. The method according to claim 6, wherein the mixed solution is prepared with stirring or under heating.

8. The method according to claim 6, wherein the organic solvent includes methanol, ethanol, isopropyl alcohol, n-propanol, isoamyl alcohol, acetone, ethyl methyl ketone, methyl isobutyl ketone, ethyl acetate, n-propyl acetate, n-butyl acetate, t-butyl acetate, toluene, dichloromethane, acetonitrile, or a mixture thereof.

* * * * *